US012178421B2

(12) United States Patent
Amanatullah et al.

(10) Patent No.: US 12,178,421 B2
(45) Date of Patent: Dec. 31, 2024

(54) SYSTEM AND METHOD FOR DETECTING, CHARACTERIZING, AND PREVENTING TISSUE DAMAGE DURING A SURGICAL PROCEDURE

(71) Applicant: The Board of Trustees of the Leland Stanford Junior University, Stanford, CA (US)

(72) Inventors: Derek F. Amanatullah, Stanford, CA (US); Hunter Storaci, Stanford, CA (US); Andrew Barrett, Stanford, CA (US); Harsh Shah, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 955 days.

(21) Appl. No.: 17/206,012

(22) Filed: Mar. 18, 2021

(65) Prior Publication Data

US 2021/0290215 A1 Sep. 23, 2021

Related U.S. Application Data

(60) Provisional application No. 62/991,546, filed on Mar. 18, 2020.

(51) Int. Cl.
*A61B 17/02* (2006.01)
*A61B 5/00* (2006.01)
*A61B 5/1455* (2006.01)
*A61B 17/00* (2006.01)
*A61B 90/00* (2016.01)

(52) U.S. Cl.
CPC .......... *A61B 17/02* (2013.01); *A61B 5/14552* (2013.01); *A61B 5/746* (2013.01); *A61B 2017/00119* (2013.01); *A61B 2090/064* (2016.02); *A61B 2560/0223* (2013.01); *A61B 2562/0219* (2013.01)

(58) Field of Classification Search
None
See application file for complete search history.

(56) References Cited

U.S. PATENT DOCUMENTS 11,786,232 B1 * 10/2023 McCandless .......... A61B 17/04
606/90
11,957,342 B2 * 4/2024 Liu .................... A61B 18/1445
(Continued)

*Primary Examiner* — Tessa M Matthews
(74) *Attorney, Agent, or Firm* — Run8 Patent Group, LLC; Peter Miller

(57) ABSTRACT

A system for monitoring potential damage to a tissue within a patient caused by tissue retraction during a surgical procedure, the system comprising: a housing body; an attachment mechanism for attaching the housing body to a tip of a surgical retractor; a force sensor; an inertial sensor; a feedback module; and a control module configured to: track force applied by the retractor tip to the tissue based on force signals received from the force sensor; detect the force applied approaching a force threshold, the force threshold based on a relationship between force applied by the retractor tip to the tissue and orientation of the retractor tip against the tissue; in response to the force applied approaching the force threshold, generating a first warning prompt indicating a possibility of damage to the tissue; and outputting the first warning prompt via a feedback module.

10 Claims, 7 Drawing Sheets

(56) References Cited

U.S. PATENT DOCUMENTS

| | | | |
|---|---|---|---|
| 2013/0123582 A1* | 5/2013 | Xia | A61B 46/17 600/202 |
| 2015/0351734 A1* | 12/2015 | Crenshaw | A61B 5/7239 606/192 |
| 2024/0081938 A1* | 3/2024 | Babu | A61B 34/30 |

* cited by examiner

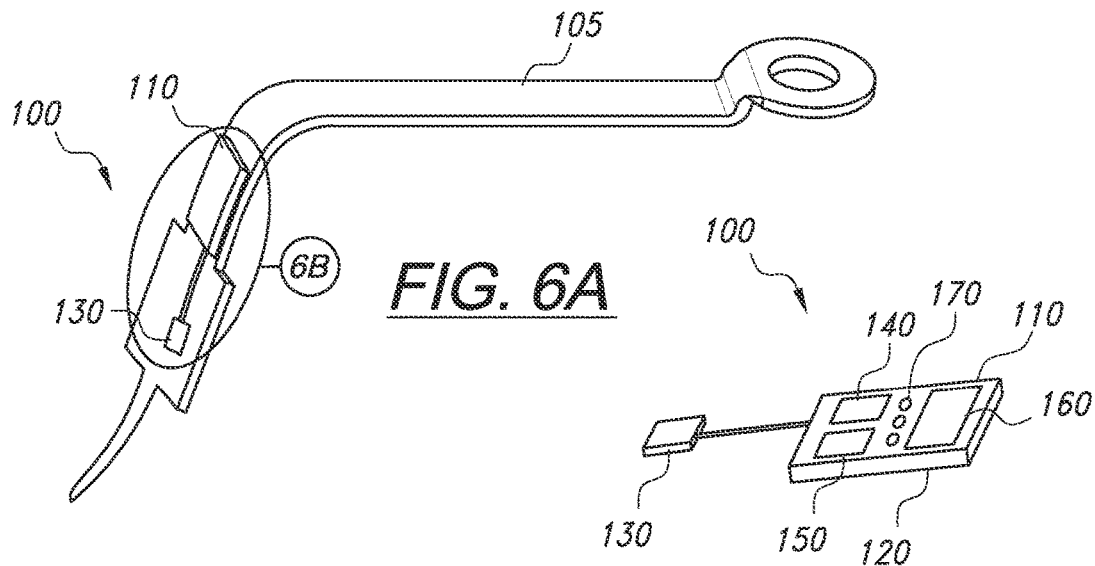
FIG. 6A
FIG. 6B
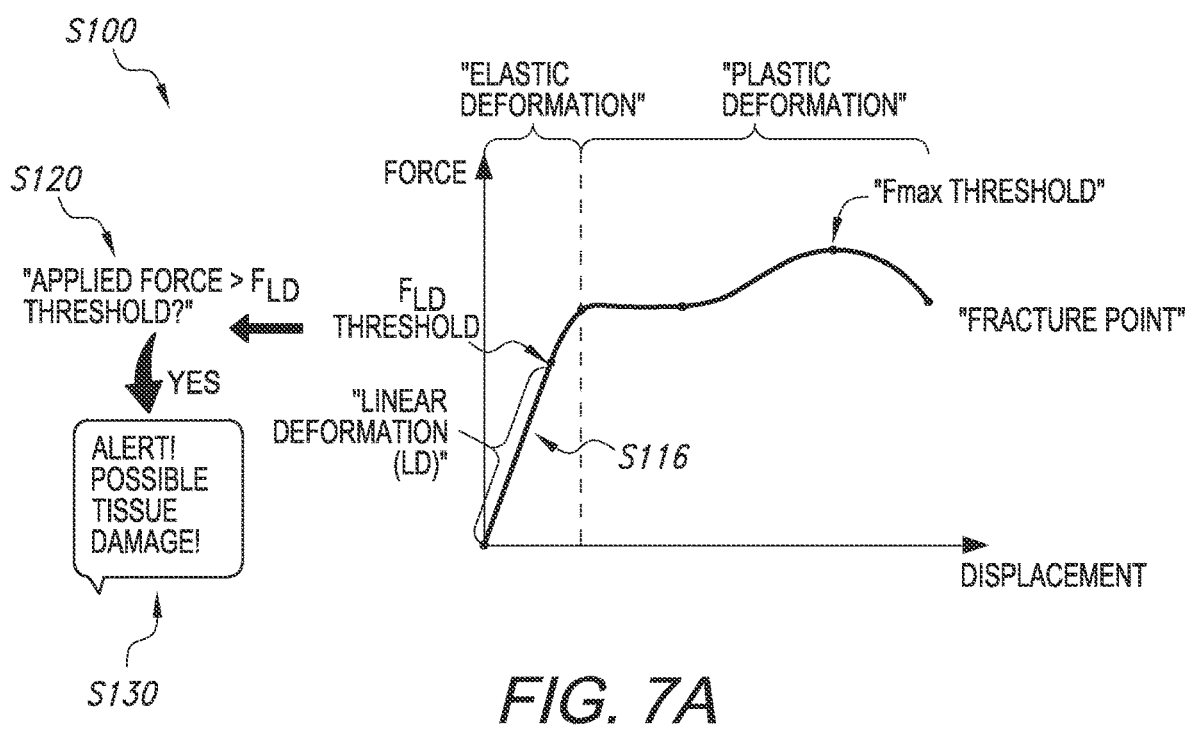
FIG. 7A

SYSTEM AND METHOD FOR DETECTING, CHARACTERIZING, AND PREVENTING TISSUE DAMAGE DURING A SURGICAL PROCEDURE

CROSS-REFERENCE TO RELATED APPLICATIONS

This Application claims priority to U.S. Provisional Patent Application No. 62/991,546, filed on 18 Mar. 2020, which is incorporated in its entiretyby this reference.

TECHNICAL FIELD

This invention relates generally to the field of surgical devices and more specifically to new and useful systems and methods for detecting, characterizing and preventing unintentional tissue damage during surgical procedures in the field of surgical devices.

BRIEF DESCRIPTION OF THE FIGURES

FIGS. 6A and 6B are a schematic representation of a fourth variation of the system;
FIGS. 7A and 7B are a flowchart representation of a method.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
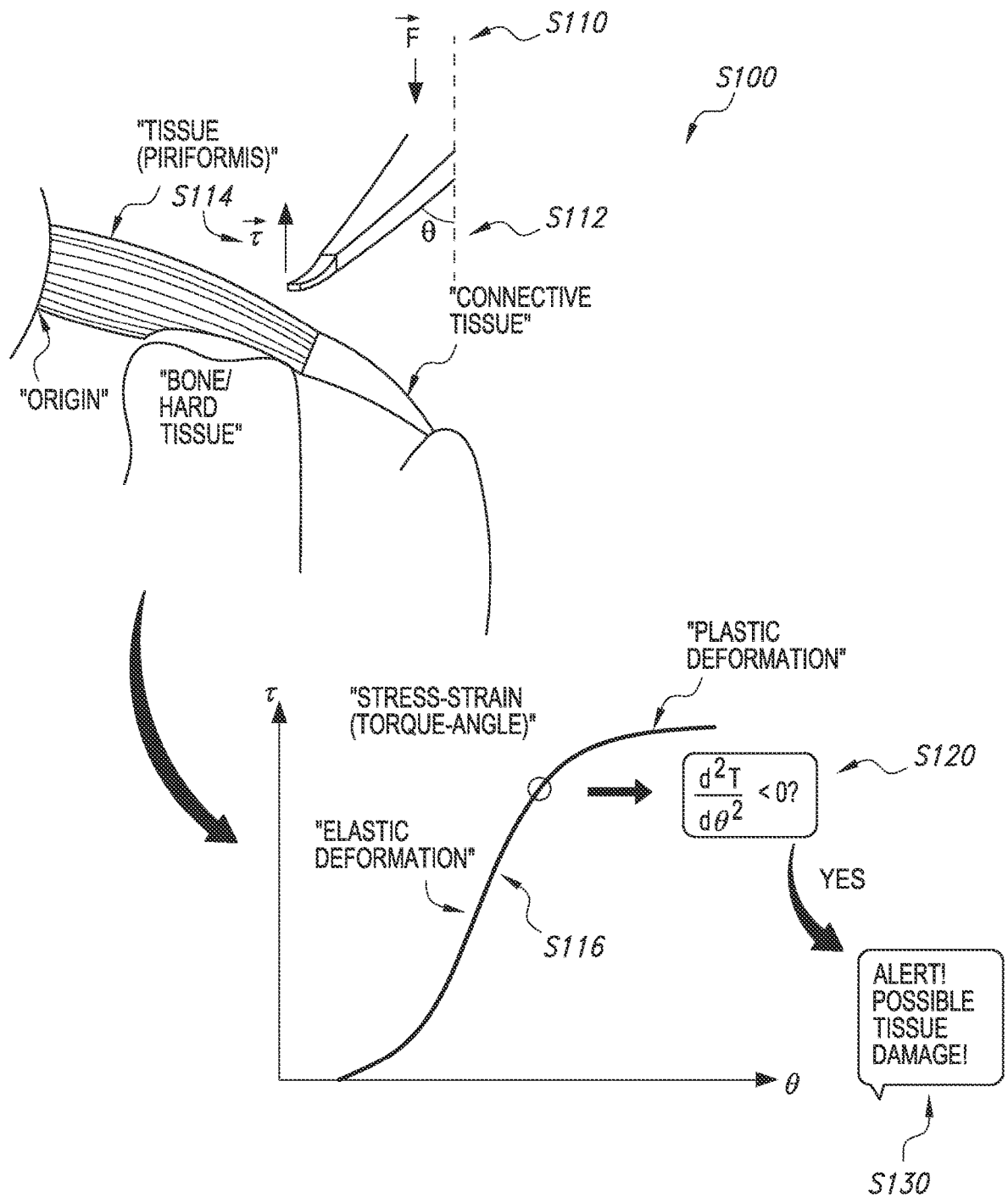
FIG. 1 is a flowchart representation of a method.

As shown in FIG. 1, a method S100 for detecting and characterizing unintentional damage caused by tissue retraction during a surgical procedure includes: during retraction of tissue over a first period of time, measuring a sequence of magnitudes of a force applied to the retractor in Block Silo; concurrently measuring a corresponding sequence of angular displacements of the retractor in Block S112; transforming the sequence of force magnitudes into a sequence of torques applied to the tissue by the retractor in Block S114; and calculating a rate of change of the applied torque as a function of the angular displacement of the retractor in Block S116; and, at a second time succeeding the first period of time, during retraction of the tissue, detecting a decrease in the rate of the change of the applied torque relative to angular displacement of the retractor in Block S120; and, in response to detecting the decrease, generating a warning prompt indicating a possibility of damage to the tissue in Block S130.

Figure 7B:
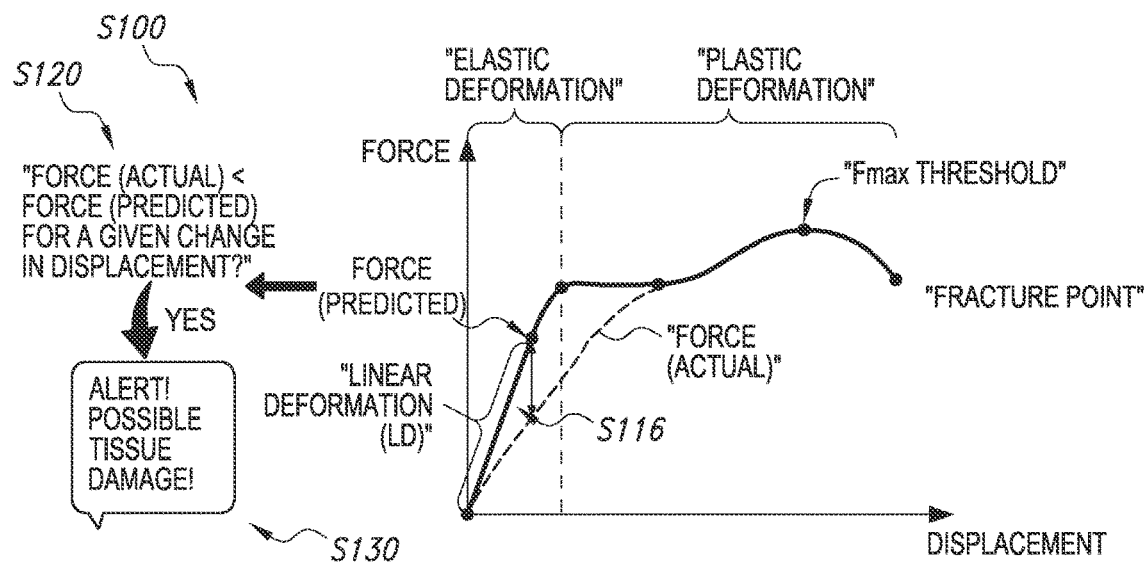

As shown in FIG. 7, one variation of the method S100 for predicting potential damage to a tissue within a patient caused by tissue retraction during a surgical procedure includes: during retraction of the tissue by a surgical retractor 105 including a retractor beam 106 and a retractor tip 107 during a first time period, outputting a sequence of force signals representing a magnitude of a force applied to the tissue via the retractor tip 107 in Block Silo; outputting a sequence of inertial signals representing orientation of the retractor tip 107 during the first time period in Block S112; tracking force magnitudes of the force applied by the retractor tip 107 to the tissue during the first time period based on the sequence of force signals; detecting the force applied by the retractor tip 107 approaching a force threshold, the force threshold based on a relationship between force applied by the retractor tip 107 to the tissue and deflection of the retractor tip 107 against the tissue; in response to the force applied by the retractor tip 107 to the tissue approaching the force threshold, generating a first warning prompt indicating a possibility of damage to the tissue; and outputting the first warning prompt.

Figure 8:
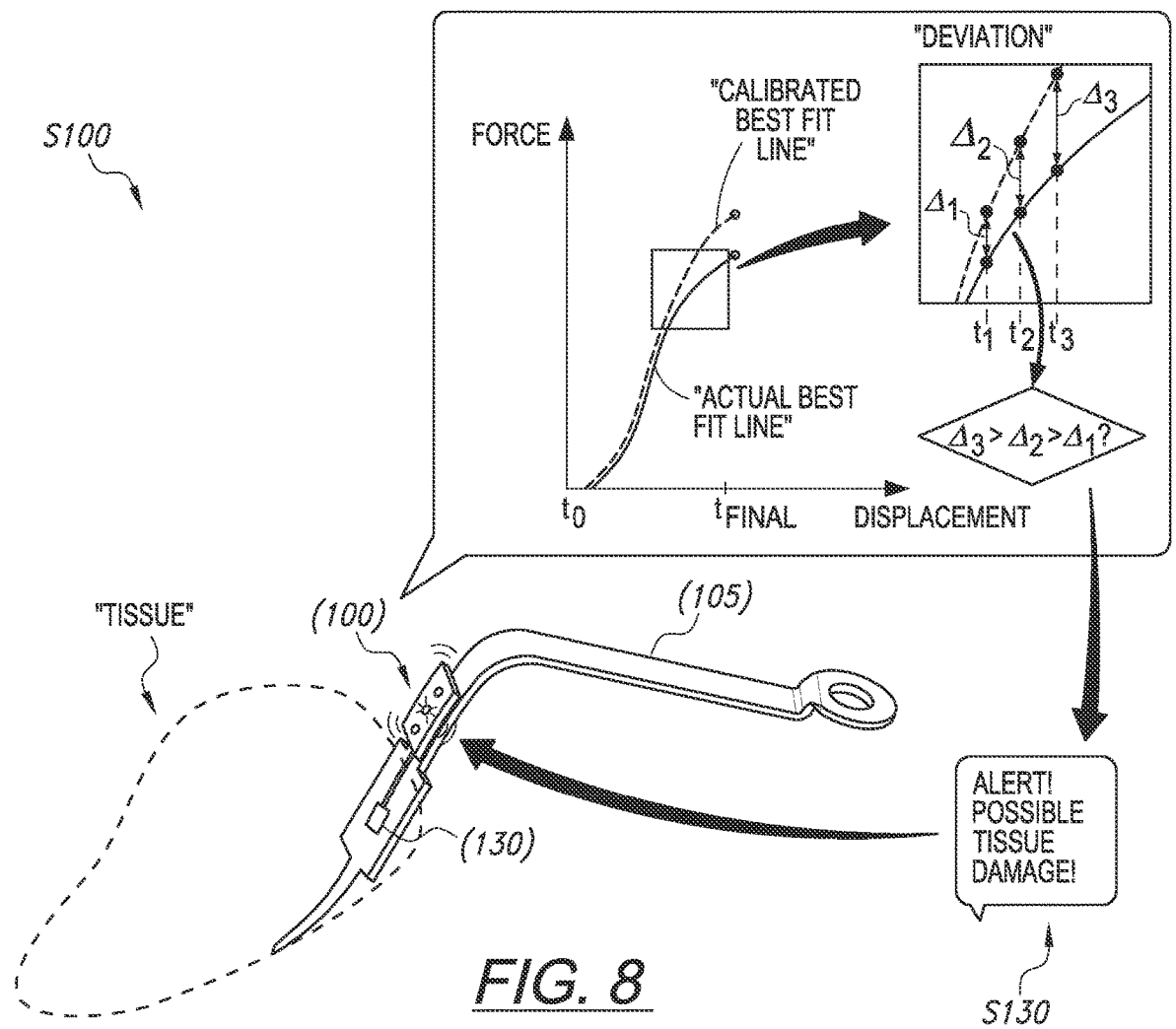
FIG. 8 is a flowchart representation of a method.

As shown in FIG. 8, another variation of the method S100 for predicting potential damage to a tissue within a patient caused by tissue retraction by a surgical retractor 105—including a retractor beam 106 and a retractor tip 107—during a surgical procedure includes: during a calibration period, outputting a first sequence of force signals representing a magnitude of a force applied to the tissue via the retractor tip 107 in Block Silo; outputting a first sequence of inertial signals representing orientation of the retractor tip 107 in Block S112; tracking a first set of force magnitudes of the force applied by the retractor tip 107 to the tissue based on the first sequence of force signals; tracking a first set of orientations of the retractor tip 107 against the tissue based on the first sequence of inertial signals; and plotting a first force-displacement curve based on the first set of force magnitudes and the first set of orientations. The method further includes: during a first time period, outputting a second sequence of force signals representing a magnitude of a force applied to the tissue via the retractor tip 107 in Block Silo; outputting a second sequence of inertial signals representing orientation of the retractor tip 107 in Block S112; tracking a second set of force magnitudes of the force applied by the retractor tip 107 to the tissue based on the second sequence of force signals; tracking a second set of orientations of the retractor tip 107 against the tissue based on the second sequence of inertial signals; plotting a second force-displacement curve based on the second set of force magnitudes and the second set of orientations; detecting the second force-displacement curve deviating from the first force-displacement curve; in response to detecting the second force-displacement curve deviating from the first force-displacement curve, generating a first warning prompt indicating a possibility of damage to the tissue; and outputting the first warning prompt.

2. Applications

Generally, the method S100 can be executed by or in cooperation with an instrumented retractor system 100 in order to prevent inadvertent damage to tissue that is retracted away from the surgeon's field of view when visualizing a surgical target. More specifically, many surgical procedures, particularly minimally invasive procedures, require tissue such as muscles, tendons, or ligaments to be moved (e.g., levered, pulled) away from their resting positions by a retractor to open a field of view in which the surgeon may visualize and operate on a target structure. However, tissue damage both inside and outside the surgeon's field of view can occur as a result of excessive displacement of the tissue during retraction and/or application of excessive force or torque by the retractor. Because the amount of retractive force sufficient to damage particular damage tendons, ligaments, muscles and/or their points of attachment is relatively small, a surgeon may unintentionally cause damage to these structures even during a minimally-invasive surgical procedure.

Thus, a retractor augmented with a set of sensors can cooperate with an on-board or external control system 100 to execute Blocks of the method S100 in order to: detect forces applied to the retractor by a surgeon during retraction of tissue; detect changes in the retractor's orientation responsive to these applied forces; characterize a relationship between applied force and retractor orientation indicative of normal elastic displacement of the retracted tissue, subsequently detect changes in this relationship between applied force and retractor orientation indicating excessive strain on the retracted tissue (e.g., reduced tissue elasticity); and generate an auditory, visual, or haptic warning to the surgeon indicating that damage to the tissue may occur if additional force is applied to the retractor, thereby enabling the surgeon to choose between intentionally damaging the tissue in order to safely complete the procedure (e.g., release or further retract the tissue to achieve the necessary field of view) or operating within a more limited field of view in order to avoid damaging the tissue.

Furthermore, an instrumented retractor can execute Blocks of the method S100 in conjunction with a control module 160 to: characterize a stress-strain relationship or force-displacement relationship for the tissue during retraction based on forces and/or torques exerted on the tissue and orientation (e.g., angular position) of the retractor; and, based on this relationship, detect, characterize, and quantify any damage to the tissue and/or associated connective structures, both inside and outside the surgical field of view, that may have been caused during retraction. The system 100 can then provide information about this damage and the extent of the damage to the surgeon during or after the procedure, thereby enabling the surgeon to: accurately assess damage caused by the operation; surgically repair damaged tissues, if feasible; recommend post-operative recovery methods (e.g., amounts and/or types of physical therapy) based on the amount of tissue damage; and correct execution of the retraction move in subsequent operations. More generally, the method S100 enables the surgeon to account for damage—or the possibility of damage—to tissues other than the target structure and when classifying a level of invasiveness of a particular surgical procedure, which can inform the surgeon's decision-making at each stage of the procedure (or subsequent procedures) in order to increase positive patient outcomes.

The method S100 is described herein as executed by or in conjunction with an instrumented, manually-operated levered retractor (e.g., a Hohmann-style retractor) applied to a *piriformis* tendon of a patient—by a surgeon—during a total hip arthroplasty in order to displace the *piriformis* tendon and thus enable the surgeon to visualize adjacent and underlying tissues. However, the method S100 can additionally or alternatively be implemented in conjunction with an instrumented retractor of the same or dissimilar geometry to monitor retraction of other muscles, tendons, or ligaments, etc., such as during a knee surgery, an elbow surgery, a shoulder surgery, a back surgery, or a surgery of any other type. For example, the method S100 can be executed by or in conjunction with an instrumented forceps-style retractor (e.g., a Meyerding-style retractor, a Gelpi-style retractor) or an instrumented malleable retractor in order to enable a surgeon to avoid or reduce unintentional tissue damage during retraction. In these examples, the method S100 can be executed by or in conjunction with an instrumented retractor to monitor and characterize retractive forces and/or to calculate ischemia times for retracted tissues and to prompt a surgeon to hold, remove, or adjust the instrumented retractor accordingly. In another example, the method S100 can also be applied to train a robotic (e.g., autonomous, semi-autonomous) surgical tool to safely perform automated retraction moves and/or executed by the robotic surgical tool during robotically-assisted surgical operations.

3. Terms

A "retractor tip" is referred to herein as a portion or end of the retractor placed in contact with tissue during retraction of that tissue. A "retractor beam" is referred to herein as the remaining portion of the retractor, and includes an end opposite the retractor tip 107 to which the surgeon may apply force to displace adjacent tissue. In particular, application of force to the retractor beam 106 (e.g., by a surgeon) effects a force, torque, and/or moment on tissue in contact with the retractor tip 107, causing the tissue to deform against the retractor tip 107.

"Elastic deformation" of tissue is referred to herein as displacement of the tissue (e.g., low to moderate displacement) such that the tissue can return to its normal (e.g., resting, equilibrium) position under a nominal, elastic, restoring force once force and/or torque on the tissue is reduced or removed.

"Non-linear deformation" is referred to herein as excessive displacement of the tissue such that elasticity of the tissue is reduced and continued application of force and/or torque to the tissue damages the tissue itself, origins of the tissue, and/or tendon or ligament connections between the tissue and other structures.

"Stress-strain relationship" is referred to herein as a relationship between stresses on a tissue (e.g., as indicated by torques applied to the tissue by a retractor, forces applied to the tissue by the retractor, and/or forces applied to the retractor by the surgeon) and strains on the tissue (e.g., indicated by orientation of the retractor, angular displacement or "tilting" of the retractor, and/or displacement of the tissue during retraction).

"Stress-strain curve" is referred to herein as a (continuous) curve or discrete plot representing a stress-strain relationship, such as displacement of a tissue as a function of: force applied to the tissue; force applied to the retractor; or torque applied to the tissue by the retractor and retractor orientation. While the method S100 is generally described herein as characterizing a stress-strain relationship based on torque applied to a tissue as a function of angular displacement (e.g., orientation) of the retractor, the system 100 can additionally or alternatively detect, calculate, and/or monitor other relationships (e.g., a stress-strain relationship) between actions taken by the surgeon and effects of these actions on tissues in order to detect, characterize, and quantify (possible) tissue damage during a retraction move.

"Force-displacement curve" is referred to herein as a (continuous) curve or discrete plot representing a force-displacement relationship, such as displacement of a tissue as a function of force applied to the tissue by the surgical retractor 105 and retractor orientation. While the method S100 is generally described herein as executed by the system 100 to characterize a force-displacement relationship based on force applied to a tissue as a function of displacement (e.g., angular orientation or linear displacement) of the retractor, the system 100 can additionally or alternatively detect, calculate, and/or monitor other relationships (e.g., a stress-strain relationship and/or pressure-displacement) between actions taken by the surgeon and effects of these actions on tissues in order to detect, characterize, and quantify (possible) tissue damage during a retraction move.

"Torque-displacement curve" is referred to herein as a (continuous) curve or discrete plot representing a toque-displacement relationship, such as displacement of a tissue as a function of torque applied to the tissue by the surgical retractor 105 and retractor orientation. While the method S100 is generally described herein as executed by the system 100 to characterize a torque-displacement relationship based on torque applied to a tissue as a function of displacement (e.g., angular orientation or linear displacement) of the retractor, the system 100 can additionally or alternatively detect, calculate, and/or monitor other relationships (e.g., a stress-strain relationship) between actions taken by the surgeon and effects of these actions on tissues in order to detect, characterize, and quantify (possible) tissue damage during a retraction move.

4. System

Generally, the system 100 includes a manually-operated levered retractor (hereinafter "the retractor"), such as the instrumented Hohmann-style retractor shown in FIG. 2. In particular, the retractor includes: a retractor beam 106 (e.g., retractor body, retractor arm) defining a rigid material with a flat edge that is configured to be placed in contact with bone or hard tissue; and a retractor tip 107 defining a similarly rigid material of smaller physical dimensions that is configured to contact muscle, tendon, ligaments, and/or other soft tissues to be retracted out of the surgical field of view. Thus, the retractor beam 106 and retractor tip 107 define a hand-held lever that leverages the bone or hard tissue (e.g., as a fulcrum) to transfer force applied to the retractor beam 106 into torque applied to tissues in contact with the retractor tip 107.

In one implementation, the retractor defines an instrumented retractor that includes a set of sensors that are attached to, affixed to, or otherwise integrated with the retractor beam 106 and/or the retractor tip 107. For example, a set of sensors—including a force sensor 130 and a distance sensor—can be integrated into the instrumented retractor during manufacturing.

Figure 2:
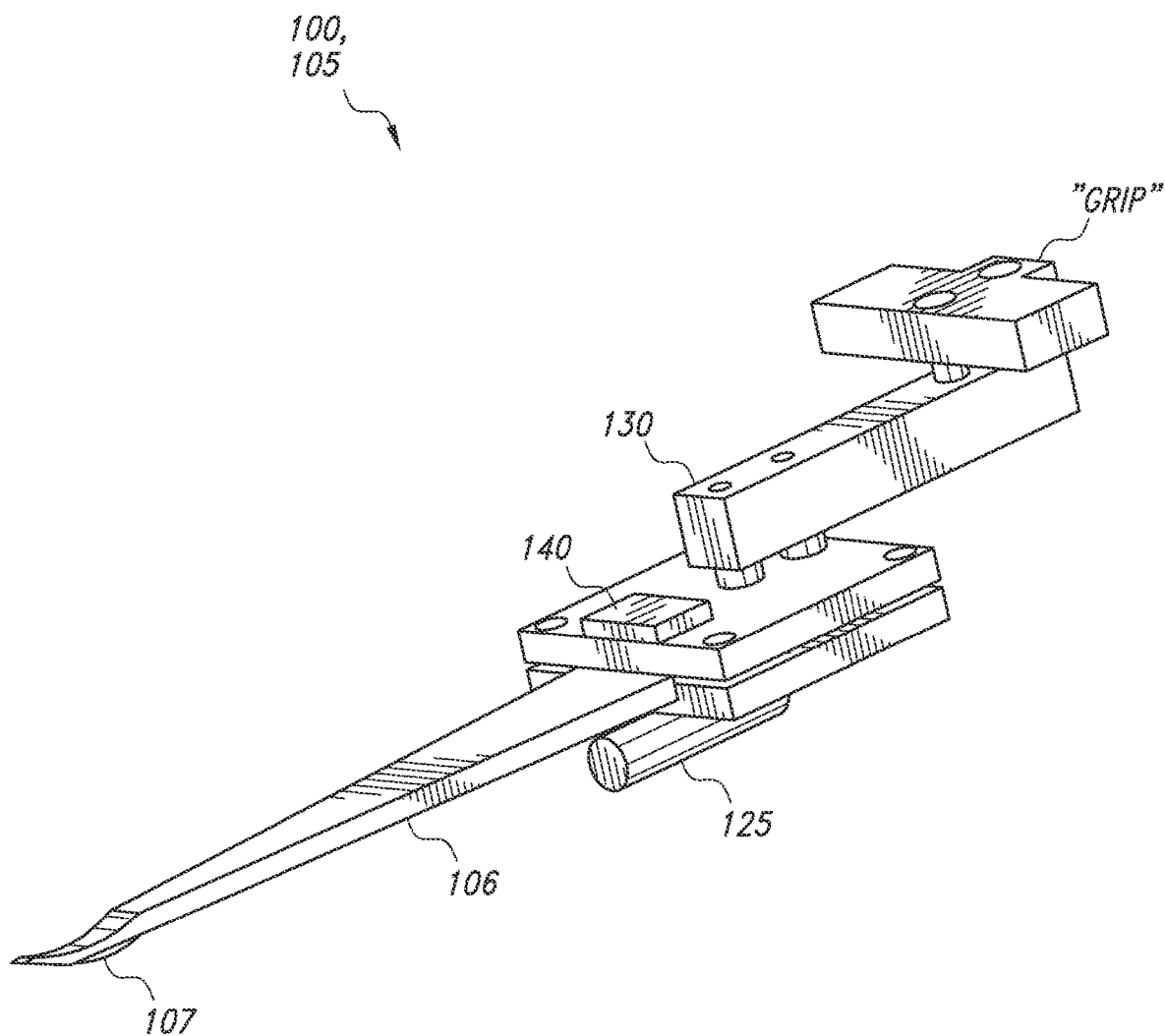
FIG. 2 is a schematic representation of a system.
Figure 3:
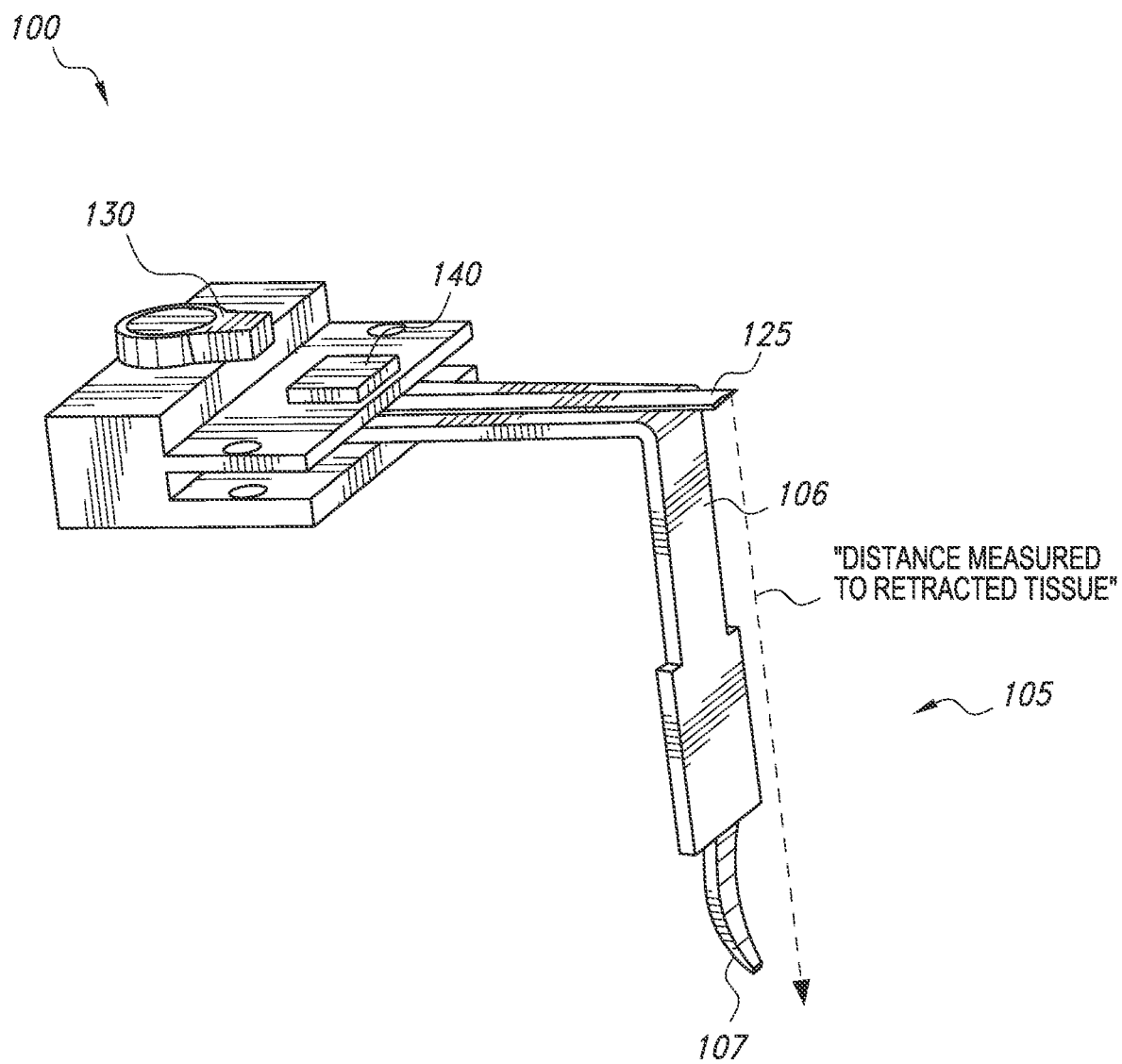
FIG. 3 is a schematic representation of a first variation of the system.

In this implementation and as shown in FIG. 2, the instrumented retractor includes: a remote distance meter 125 configured to detect a distance between the end of the retractor beam 106 and the fulcrum (e.g., distance to the bone) along the axis of the retractor; a force sensor; an accelerometer and/or gyroscope 140 configured to detect the position, orientation and/or angular displacement of the retractor relative to the fulcrum; and a grip attached or affixed to the end of the retractor beam 106. In one example, the force sensor 130 defines a load cell affixed to the end of the retractor that includes a set of mechanical and/or electrical force-sensitive components (e.g., strain gauges and/or force-sensitive resistive elements) configured to continuously or intermittently track force applied to the retractor beam 106 (e.g., by a surgeon). In another example, these force-sensitive components are affixed to and/or integrated into the retractor tip 107 and are thus configured to directly detect magnitudes of forces applied to tissues by the retractor tip 107. Generally, the grip can include haptic and/or auditory feedback modules that are configured to output vibratory and/or audio signals in response to detecting damage or potential damage to retracted tissues. In this implementation, the instrumented retractor can also include an input mechanism, such as a trigger or a shock, configured to enable (e.g., initiate) recording of data capture by the load cell 130, accelerometer/gyroscope 140, and the remote distance meter 125. For example, the surgeon may: depress the input mechanism when initiating the retraction move and/or during execution of the retraction move in order to enable data capture of force, orientation, and distance data during this retraction move; and then release the input mechanism when repositioning the retractor, thereby releasing application of force to the retractor beam 106 and thus preventing false-positive feedback.

The instrumented retractor also includes (and/or cooperates with) a control module 160 and a feedback module 150. The control module 160 is configured: to sample force, distance, and orientation data from the set of sensors (e.g., at a rate of 100 Hz); to track displacement of an adjacent tissue in contact with a tip of the retractor based on output of the distance sensor; to characterize force and/or torque applied to the adjacent tissue as a function of displacement of the tissue, applied force measured by the force sensor 130, and/or orientation of the retractor; and to trigger the feedback module 150 in response to a relationship between displacement of the adjacent tissue and force and/or torque applied to the adjacent tissue indicating (possibility of) damage to the adjacent tissue.

In one example, the control module 160 defines an external computer system configured to receive data from a set of wireless transceivers on the instrumented retractor 105 and accordingly execute Blocks of the method S100. In another example, the control module 160 defines a microcontroller or other logic devices located on the retractor and connected (e.g., via wired connections, via wireless connections) to the set of sensors.

In another implementation, the set of sensors is integrated into a modular, peripheral attachment 100 that can be affixed to an existing base retractor 105 before or during a surgical procedure. The peripheral attachment can include: a remote distance meter 125; a force sensor 130 configured to track the magnitude of a force applied to the retractor (e.g., at the point of contact with the surgeon); a level or gyroscope 140 configured to track the orientation of the retractor beam 106; and a set of wireless transceivers configured to transmit force, orientation, and distance data to an external computer system configured to execute Blocks of the method S100. Following the procedure, the peripheral attachment 100 can be disposed of and the base retractor 105 sanitized in preparation for a subsequent surgery.

In a similar implementation, a system 100 for predicting potential damage to a tissue within a patient caused by tissue retraction can be affixed to an existing surgical retractor 105 before or during a surgical procedure. In particular, the system 100 includes: a housing body no; an attachment mechanism 120 configured to attach the housing body 110 to the surgical retractor 105 (e.g., via a magnet, a strap, an adhesive, a silicone tubing that encloses at least a portion of the surgical retractor 105), the surgical retractor 105 including a retractor beam 106 and a retractor tip 107 at a distal end of the retractor beam 106; a force sensor 130 configured to output a force signal representing a magnitude of a force applied to the tissue via the retractor tip 107; an inertial sensor 140 configured to output an inertial signal representing orientation of the retractor tip 107 (e.g., an inertial measurement unit, a gyroscope, and/or a tilt sensor); and a feedback module 150. The system 100 further includes a control module 160 configured to: track force magnitudes of the force applied by the retractor tip 107 to the tissue during a first time period based on the force signal received from the force sensor 130; detect the force applied by the retractor tip 107 approaching a force threshold, the force threshold based on a relationship between force applied by the retractor tip 107 to the tissue and deflection of the retractor tip 107 against the tissue; in response to the force applied by the retractor tip 107 to the tissue approaching the force threshold, generating a first warning prompt indicating a possibility of damage to the tissue; and outputting the first warning prompt via the feedback module 150 (for example, in conjunction with a set of LED indicators 170). Following the procedure, the system 100 can be disposed of and the base retractor sanitized in preparation for a subsequent surgery. In one implementation, the system 100 includes a set of paired dongles that can be positioned at different locations on the surgical retractor 105, the paired dongles including the same set of components or different components distributed across the dongles.

5. Data Capture Activation

In one implementation, the system 100 can selectively capture data from the force sensor 130 and the inertial sensor 140 to reduce and/or minimize unwanted data collection during preparation and/or performance of a surgical procedure, thereby improving the quality of data captured for more accurate calibration and inter-operative detection of tissue damage and reducing the possibility of triggering a false alert for damage to a retracted tissue. In addition, the system 100 can provide a hands-free method for activating data capture, thus eliminating the need for the surgeon to activate (e.g., by pushing a button, flipping a switch, or other similar methods) it herself and freeing her hands for other aspects of the surgical procedure.

In particular, the system 100 can include a set of conductive tabs arranged on the housing body 110 and/or the force sensor 130; wherein the control module 160 is further configured to: track impedance values across the set of conductive tabs and, in response to detecting a reduction in impedance values from a first sampling interval to a second sampling interval, initiate capture of the force sensor 130 and the inertial sensor 140. The system 100 interprets a reduction in impedance values across the conductive tabs as an indication that the conductive tabs have come into contact with patient tissue (e.g., generally, human tissue has a certain amount of moisture that can complete an electrical circuit between conductive tabs).

Additionally and/or alternatively, the system 100 can include a motion sensor configured to output a motion signal based on detected motion of the system 100; wherein the control module 160 is further configured to initiate capture of the force sensor 130 and the inertial sensor 140 based on the motion signal. For example, the system 100 can capture data from the force sensor 130 and the inertial sensor 140 based on a series of movements that indicate that the system 100 has been positioned against retracted tissue (e.g., detected motion of the system 100 and a subsequent lack of motion of the system 100; More specifically, the system 100 generally does not move once the tissue is retracted and thus a lack of motion indicates that the system 100 has been positioned against retracted tissue). In addition, the system 100 can pause capturing data from the force sensor 130 and the inertial sensor 140 based on a series of movements that indicate that the system 100 has been removed from the retracted tissue (e.g., detected motion of the system 100 after a period of lack of motion of the system 100). The system 100 may determine a motion threshold for the motion signal such that slight motion of the system 100 (e.g., a patient's breathing or heartbeat may cause some movement of the system 100 during a surgical procedure) does not interrupt data capture from the force sensor 130 and the inertial sensor 140.

Additionally and/or alternatively, the system 100 can capture data from the force sensor 130; in response to a force signal output by the force sensor 130 exceeding a first force load threshold, the system 100 can interpret that the surgical retractor 105 has come into contact with patient tissue. Further, in one example, the system 100 can interpret that the surgical retractor 105 has come into contact with patient tissue in response to a set of force signals output by the force sensor 130 exceeding the first force load threshold for a minimum threshold of time (e.g., the set of force signals exceed 2 Newtons for a minimum of 1 second). More specifically, the system 100 can: filter the force signals output by the force sensor 130; and select a subset and/or time period of force signals for calibration and/or inter-operative detection of tissue damage. Additionally and/or alternatively, in response to a force signal output by the force sensor 130 exceeding a second force load threshold, the system 100 can interpret that the surgical retractor 105 has come into contact with a surface other than patient tissue (for example, if the surgical retractor is displaced or falls); and the system 100 can pause capturing data from the force sensor 130.

6. Tracking Force & Angular Displacement

In one implementation, the system 100 tracks force magnitudes of the force applied by the retractor tip 107 to the retracted tissue (e.g., based on force signals by force sensor 130 in contact with the retracted tissue); and tracks deviations in orientation of the retractor tip 107—against the retracted tissue (e.g., based on inertial signals by inertial sensor 140)—from a natural position of the tissue.

The system 100 calculates angular displacement (i.e., deflection) of the retractor tip 107 based on a change in orientation of the retractor tip 107—from its natural position (i.e., without deflection)—as the retractor is tightening against a target tissue during the surgical procedure. Based on these force magnitudes and orientations, the system 100 can: plot a force-displacement curve; monitor a force magnitude applied to the retracted tissue; and generate and transmit a warning prompt in response to the applied force approaching, meeting, and/or exceeding a determined force threshold, indicating possible damage to the retracted tissue.

For example, the system 100: can include a pair of offset electrodes arranged on a surface of the body and coupled to an interrupt pin on the control module 160; and can transition from a hibernate or low-power mode into an active mode in response to a drop in impedance across these two electrodes, which may occur when the electrodes contact a conductive fluid (e.g., blood, saline). Thus, when the surgeon retrieves the system 100 and places the system 100 in contact with the target tissue, the impedance across the two electrodes may drop, thereby triggering the control module 160 to activate. Once active, the control module 160 can: sample an initial set of orientation values from the inertial sensor 140 (e.g., an accelerometer, a tilt sensor), such as over a two-second interval; and sample an initial set of force magnitudes from the force sensor 130 over this same interval immediately following contact between the body of the system 100 and the target tissue. The control module 160 can then: average the initial set of orientation values to calculate a natural or "starting" orientation; and average the initial set of force magnitudes to calculate a baseline force magnitude for the current application of the system 100. Subsequently, the control module 160 can: sample additional orientation values from the inertial sensor 140; subtract the natural orientation from these orientation values to calculate a timeseries of angular displacements at the retractor tip 107; sample additional force magnitudes from the force sensor 130; and subtract the baseline force magnitude from these force magnitudes to calculate a timeseries of normalized force magnitudes applied to the target tissue. The control module 160 can then implement methods and techniques described below to calibrate a force-displacement curve (e.g., a force magnitude versus angular displacement curve) and/or predict damage to the target tissue based on the timeseries of normalized force magnitudes and the timeseries of angular displacements.

6.1 Calibration

Generally, a surgeon (and/or another member of the surgical team) calibrates the system 100 before and/or during a surgical procedure to improve the accuracy of data capture by the system 100 (e.g., force signals, inertial signals), to determine a modulus of elasticity of a tissue being retracted, and/or to calculate thresholds for retractive force that can be applied to the retracted tissue. The modulus of elasticity and thresholds can vary based on the type of tissue that is retracted, a position of the system 100 against the tissue, and/or the age and/or medical history of the patient undergoing the surgical procedure. More specifically, the system 100 can be calibrated for a particular position against a particular tissue within a particular patient to prevent and/or minimize potential damage to a retracted tissue caused by a surgical retractor 105 during the surgical procedure.

During a calibration process, a surgeon may initiate a retraction move by positioning the surgical retractor 105 against the tissue to be retracted and applying force to the surgical retractor 105 to retract the tissue (e.g., a low force magnitude to prepare the tissue for further retraction after the calibration period). The surgeon may then remove the surgical retractor 105 and return the retracted tissue to its resting position (e.g., reverse the initial retraction move). By removing the surgical retractor 105, the surgeon may facilitate the tissue in acclimating to unnatural movement and prepare the tissue for its retracted position during the surgical procedure. After this calibration process, the surgeon may execute a second retraction move (similar to the initial retraction move) to position the surgical retractor 105 and retract the tissue from the surgeon's field of view for the surgical procedure.

Blocks of the method S100 recite: during a calibration period preceding the first time period (i.e., a time period during performance of the surgical procedure): tracking force magnitudes of the force applied by the retractor tip 107 to the tissue during the calibration period based on the sequence of force signals; tracking orientations of the retractor tip 107 against the tissue during the calibration period based on the sequence of inertial signals; and plotting a force-displacement curve based on the force magnitudes and the orientations.

In particular, the control module 160 is configured to, during the calibration period preceding the first time period (i.e., a time period during performance of the surgical procedure): track force magnitudes of the force applied by the retractor tip 107 to the tissue during the calibration period based on the force signal received from the force sensor 130; track orientations of the retractor tip 107 against the tissue during the calibration period based on the inertial signal received from the inertial sensor 140; and plot a force-displacement curve based on the force magnitudes and the orientations.

During the initial retraction move, as a retractor tip 107 of the surgical retractor 105 contacts the tissue, the force sensor 130 outputs a set of force signals, each representing a magnitude of a force applied to the tissue via the retractor tip 107 of the surgical retractor 105, and the inertial sensor 140 concurrently outputs a set of inertial signals, each representing orientation of the retractor tip 107. Based on the initial data from the force sensor 130 and the inertial sensor 140 during the initial retraction move, the control module 160 can plot a force-displacement curve.

To plot the force-displacement curve, the control module 160 can derive a best-fit line based on the force magnitudes of the force applied by the retractor tip 107 to the tissue during the calibration period based on the sequence of force signals and on the orientations of the retractor tip 107 against the tissue during the calibration period based on the sequence of inertial signals. The control module 160 can plot the orientations (e.g., along an x-axis) and the force magnitudes (e.g., along a y-axis); and implement techniques (e.g., linear regression, least squares method, or other suitable methods) to derive a linear function that best fits the data of the plot. Accordingly, this linear function represents a region of linear deformation on the force-displacement curve for the retracted tissue, a region in which the retracted tissue undergoes only elastic deformation (i.e., the retracted tissue deforms under an applied force and then returns to its original state after the applied force is removed). The slope of the linear function indicates a relationship between an amount of displacement of the surgical retractor 105 and a force magnitude applied to the tissue (i.e., similar to a modulus of elasticity or "Young's Modulus" on a stress-strain curve). For example, the slope of the linear function for a particular tissue may carry units in Newtons (of force applied to the tissue by the retractor tip 107) per degree (of displacement of the retractor tip 107 relative to its baseline position).

The control module 160 can then employ the force-displacement curve (in particular, the linear region of the force-displacement curve) to detect deviations in subsequent force-displacement values during the surgical procedure from the initial force-displacement curve and/or predict and/or set thresholds (e.g., for a point at which the tissue transitions from linear deformation to non-linear deformation, for a maximum force to be applied to the retracted tissue, for a predicted force based on data from prior surgical procedures, and/or for a level of deviation between subsequent force-displacement values from the initial force-displacement curve).

In one implementation, the control module 160 can apply a safety factor to the calculated threshold (i.e., reduce the threshold by a defined percentage or number) to reduce a possibility of damage to the retracted tissue by the surgical retractor 105. For example, the control module 160 can set the safety factor at 0% for a standard surgery, at 10% for a surgery on an elderly person (in which damage to retracted tissue and/or surgical complications may be more likely to occur and/or post-surgical healing and recovery may occur more slowly), at 20% for a surgery on an elite athlete (in which preserving optimal health and performance of the patient's tissue(s) and/or minimizing post-surgical healing and recovery times are a high priority), at 30% for a surgery on a patient with a degenerative muscle disease (in which severe damage to retracted tissue and/or surgical complications may be more likely to occur and/or post-surgical healing and recovery may occur more slowly), or at −10% for an emergency surgery on a patient (e.g., a patient in a high-risk scenario in which preserving the patient's life has a higher priority than minimizing damage to the patient's retracted tissue(s)). In one implementation, the control module 160 can receive a safety factor as input from a surgeon (e.g., the surgeon may determine a suitable safety factor for a patient based on the patient's medical history and/or parameters). By applying a safety factor, the control module 160 can generate a warning prompt for the surgeon at lower force magnitudes applied to the retracted tissue and minimize the likelihood of causing damage to the retracted tissue.

The control module 160 can calculate one or more of the following thresholds described herein, alone or in some combination thereof. In one implementation, the control module 160 can implement one or more thresholds as a redundant safety precaution to minimize the likelihood that the surgical retractor 105 causes damage to the retracted tissue that goes undetected by the system 100.

6.1.1 Linear Deformation Force Threshold

In one implementation, the control module 160 can: plot the force-displacement curve; and calculate a linear deformation force threshold indicating a force magnitude applied to the retracted tissue at which the tissue can transition from experiencing linear deformation to non-linear deformation. By calculating the linear deformation force threshold, the control module 160 can: set the limit for a force magnitude to be applied to a retracted tissue; detect if the applied force to the retracted tissue approaches, nears, or meets the force threshold; and generate and transmit a warning prompt to the surgeon to remove, adjust, and/or modify the position of the surgical retractor 105 against the retracted tissue, thereby minimizing the likelihood of non-linear deformation occurring to the retracted tissue (i.e. irreversible deformation that could potentially cause permanent pain and/or discomfort for the patient, increase healing and recovery times for the patient, and/or increase the possibility of future, more severe injury to the tissue).

In particular, in one implementation, the control module 160 is configured to, during a calibration period preceding the first time period (i.e., a time period during performance of the surgical procedure): track force magnitudes of the force applied by the retractor tip 107 to the tissue during the calibration period based on the force signal received from the force sensor 130; track orientations of the retractor tip 107 against the tissue during the calibration period based on the inertial signal received from the inertial sensor 140; plot a force-displacement curve based on the force magnitudes and the orientations; and calculate the force threshold (e.g., linear deformation force threshold) based on the force-displacement curve, the force threshold indicating an onset of non-linear deformation of the tissue.

To calculate the linear deformation force threshold based on the force-displacement curve, the control module 160 can: retrieve a modulus of elasticity (i.e., Young's Modulus) and a yield strength value for a particular tissue (e.g., from known research data on stress-strain properties of the tissue); calculate a relationship (e.g., a scalar value) between the modulus of elasticity and the slope of the best-fit line of the force-displacement curve; and estimate the linear deformation force threshold by transforming the yield strength value using the calculated relationship (e.g., multiplying the yield strength value by the scalar value).

Additionally and/or alternatively, the control module 160 can generate a predictive model based on data (stress-strain and/or force-displacement) for a particular tissue during previous procedures and/or known research data; receive a set of patient factors (e.g., input by a surgeon or medical staff, or imported from a patient chart or database), such as gender, age, medical history, tissue type (e.g., muscle, ligament, organ, etc.), tissue location, and other relevant factors; input the set of patient factors into the predictive model; and calculate the linear deformation force threshold on the force-displacement curve for the retracted tissue.

In another implementation, the control module 160 can receive a predefined linear deformation force threshold (e.g., input by a surgeon via a user interface) during the calibration process (for example, if the surgeon prefers to take certain precautions based on knowledge from prior procedures on other patients and/or of particular aspects of a patient's medical history).

Blocks of the method S100 recite: during a calibration period preceding the first time period (i.e., a time period during performance of the surgical procedure): tracking force magnitudes of the force applied by the retractor tip 107 to the tissue during the calibration period based on the sequence of force signals; tracking orientations of the retractor tip 107 against the tissue during the calibration period based on the sequence of inertial signals; plotting a first force-displacement curve based on the force magnitudes and the orientations; and calculating the force threshold based on the first force-displacement curve, the force threshold indicating an onset of non-linear deformation of the tissue.

Accordingly, the control module 160 can: calculate the linear deformation force threshold; store the calculated force threshold as a threshold value; and generate and transmit a warning prompt to a surgeon during surgery if the applied force to the retracted tissue approaches, nears, or meets the linear deformation force threshold.

6.1.2 Maximum Force Threshold

Additionally or alternatively, the control module 160 can: calculate a maximum force threshold indicating a force magnitude applied to the retracted tissue at which the tissue will experience a maximum possible amount of stress, a point at which the tissue can transition from experiencing strain hardening to necking (which corresponds to an "ultimate strength" point on a stress-strain curve) and leading to an eventual fracture/tear of the tissue. During a particularly challenging surgical procedure, a surgeon may need to weigh the risks and benefits of causing mild to moderate damage to a retracted tissue in order to complete the surgical procedure and, therefore, may choose to disregard a first warning prompt that indicates that the retracted tissue is nearing or is exhibiting non-linear deformation behavior (e.g., a surgeon may prioritize saving the life of a trauma patient in the ER over minimizing damage to a retracted tissue) and may need an additional warning prompt that indicates that the retracted tissue is nearing a fracture point and/or tear.

Accordingly, the control module 160 can: set the limit for a maximum force magnitude to be applied to a retracted tissue based on the maximum force threshold (e.g., after the applied force to the tissue exceeds the linear deformation force threshold); detect if the applied force to the retracted tissue approaches, nears, or meets the maximum force threshold; and generate and transmit a warning prompt to the surgeon to remove, adjust, and/or modify the position of the surgical retractor 105 against the retracted tissue, thereby minimizing the likelihood of severe damage occurring to the retracted tissue (e.g., that could affect a quality of life of the patient and/or be life-threatening).

In one example, the control module 160 can implement the maximum force threshold, for example, if the applied force to the retracted tissue has already exceeded the linear deformation force threshold (e.g., as an additional safety precaution). In another example, the control module 160 can, in response to detecting the applied force to the retracted tissue exceeding the linear deformation force threshold, calculate the maximum force threshold; and then subsequently implement the maximum force threshold (i.e., put an additional force threshold in place only when deemed necessary). The control module 160 can output a second warning prompt indicating that the applied force is approaching, meeting, and/or exceeding the maximum force threshold via the feedback module 150 (e.g., by an auditory, visual, and/or haptic signal, which can differ from the signal corresponding to the first warning prompt indicating that the applied force is approaching, meeting, and/or exceeding the linear deformation force threshold).

In another implementation, the control module 160 can determine a total amount of retractive force applied to the tissue during a time period in which the retracted tissue is experiencing non-linear deformation. By accumulating the amount of retractive force causing non-linear deformation, the control module 160 can identify if a retracted tissue is nearing a fracture point. The control module 160 can set a maximum force threshold based on data regarding fracture points of particular tissues from known research and/or previous procedures. Blocks of the method S100 recite: calculating a maximum force threshold for a total amount of retractive force applied to the tissue during a non-linear deformation time period based on the first force-displacement curve, the non-linear deformation time period subsequent to detecting the force applied by the retractor tip 107 to the tissue exceeding the force threshold, the maximum force threshold indicating a fracture point of the tissue; and summing force magnitudes applied by the retractor tip 107 to the tissue during the non-linear deformation time period; determining the total amount of retractive force applied to the tissue during the non-linear deformation time period based on the summation of force magnitudes; and generating a second warning prompt in response to detecting the total amount of retractive force approaching the maximum force threshold.

Accordingly, the control module 160 can: calculate the maximum force threshold; store the calculated force threshold as a threshold value; and generate and transmit a warning prompt to a surgeon during surgery if the applied force to the retracted tissue approaches, nears, or meets the maximum force threshold.

6.1.3 Historical Data-Driven Threshold

Additionally and/or alternatively, the control module 160 can calculate a force threshold based on data (e.g., stress-strain and/or force-displacement) generated for the particular tissue during previous procedures. For example, the control module 16o can: access a database (e.g., from cloud storage, from local memory) containing data generated during retraction of the particular tissue in previous operations on patients of a similar demographic (e.g., age, gender, weight); identify a subset of data corresponding to procedures in which tissue damage occurred during retraction (e.g., based on stress-strain and/or force-displacement curves generated during each procedure); and set the threshold based on force magnitudes observed to cause and/or correspond to tissue damage (e.g., an average magnitude, the lowest magnitude). Thus, the control module 160 can output a warning prompt via the feedback module 150 in response to detecting an applied force to the retracted tissue that approaches or exceeds a force threshold observed to be associated with tissue damage in previous procedures, even if the control module 160 has not yet detected tissue damage (e.g., non-linear deformation) during the current procedure. In one example, the control module 160 can store data generated during current surgical procedures to further build the database and improve the accuracy of the set of calculated force thresholds for future surgical procedures (e.g., for patients with a particular set of demographics and/or a particular type of retracted tissue). In particular, the control module 160 can transmit the force and orientation data during the course of the surgical procedure, the set of force thresholds used during the surgical procedure, a type of tissue that is retracted (e.g., muscle, tendon, ligament), demographics of the patient (e.g., age, gender, weight), surgical events during the procedure (e.g., resetting and/or repositioning of the surgical retractor 105, force thresholds exceeded, warning prompts generated and/or transmitted), and surgical outcomes of the procedure (e.g., patient recovery status and time for recovery) to the database for storage. Therefore, the system 100 can calculate force thresholds for a particular surgery with improved accuracy and for improved patient outcomes.

Blocks of the method S100 recite: accessing force-displacement data generated during retraction of the particular tissue in previous surgical procedures on patients of a similar demographic; identifying a subset of force-displacement data corresponding to procedures in which tissue damage occurred during retraction; setting a second force threshold based on force magnitudes observed to correspond to an occurrence of damage to the tissue; generating a second warning prompt in response to detecting a force applied to the retracted tissue approaching the second force threshold, the second warning prompt indicating damage to the tissue; and transmitting the second warning prompt (e.g., via the feedback module 150), the second warning prompt differing from the first warning prompt (e.g., by auditory, visual, and/or haptic means).

6.1.4 Best-Fit Line Deviation Threshold

Additionally and/or alternatively, the control module 160 can: calculate a deviation threshold indicating an amount of deviation between the linear deformation region of the force-displacement curve calculated during calibration and force-displacement values captured during a surgical procedure (i.e., the slope of the best-fit line calculated during calibration serves as a baseline, and a deviation from the baseline during the surgical procedure can indicate that the retracted tissue is undergoing non-linear deformation). In particular, the control module 160 can set a deviation threshold as a percentage number (e.g., 2%, 5%, 10%, etc.)

or receive the deviation threshold as input by a surgeon (e.g., via a user interface); calculate a deviation of force-displacement values at a first sampling interval during the surgical time period from the best-fit line; and generate and transmit a warning prompt in response to detecting the calculated deviation exceeding the deviation threshold.

Additionally and/or alternatively, the control module 160 can detect an amount of deviation between the linear deformation region of the force-displacement curve calculated during calibration and force-displacement values captured during a surgical procedure; detect a concurrent change in displacement; and generate and transmit a warning prompt in response to detecting that an actual force applied to the retracted tissue does not match an expected force for a given amount of change in displacement of the retractor tip 107. In particular, the control module 160 can detect that the actual force applied to the retracted tissue is less than the predicted force (e.g., based on the force-displacement curve calculated during calibration), thereby indicating plastic deformation of the retracted tissue.

Blocks of the method S100 recite: tracking orientations of the retractor tip 107 against the tissue during the first time period (e.g., during the surgical procedure) based on the sequence of inertial signals; plotting a second force-displacement curve based on the force magnitudes and the orientations during the second time period (a subsequent time period during the surgical procedure); and, in response to the second force-displacement curve deviating from the first force-displacement curve, generating a second warning prompt, and outputting the second warning prompt.

In another implementation, the control module 160 can implement a continuous feedback loop of detecting a deviation of force-displacement values at multiple sampling intervals during the surgical procedure from force-displacement values of the best-fit line (i.e., linear region of the force-displacement curve from the calibration process); and generate and transmit a warning prompt indicating that the deviation is increasing over the surgical time period, indicating that the retracted tissue is likely experiencing non-linear deformation. For example, the control module 160 can: detect a first deviation between force-displacement values at a first sampling interval during the surgical procedure; detect a second deviation between force-displacement values at a second sampling interval during the surgical procedure; and, in response to the second deviation exceeding the first deviation, generate and transmit a warning prompt to the surgeon via the feedback module 150. In one implementation, the control module 160 can implement a deviation threshold for a predefined amount that the second deviation exceeds the first deviation (e.g., 1% deviation increase, 2% deviation increase, etc.).

Blocks of the method S100 recite: detecting the second force-displacement curve deviating from the first force-displacement curve by detecting a first deviation between the first force-displacement curve and the second force-displacement curve at a first sampling interval during the first time period; detecting a second deviation between the first force-displacement curve and the second force-displacement curve at a second sampling interval succeeding the first sampling interval during the first time period, the second deviation exceeding the first deviation; and, wherein generating the first warning prompt indicating the possibility of damage to the tissue includes generating the first warning prompt indicating the possibility of damage to the tissue based on the second deviation exceeding the first deviation.

In one implementation, the system 100 can implement the deviation threshold as a redundant safety precaution in addition to one or more of the above threshold methods described herein, thereby minimizing the possibility of inadvertent damage occurring to the retracted tissue.

6.2 Inter-Operative Tracking

During a surgical procedure, the system 100 monitors a force magnitude applied to a retracted tissue by a surgical retractor 105 (e.g., via force signals by the force sensor 130 and inertial signals by the inertial sensor 140); calculates whether the force applied is approaching, meeting, and/or exceeding a force threshold (e.g., one or more of the force thresholds described herein that are set during a calibration process of the system 100); in response to the applied force approaching, meeting, and/or exceeding the force threshold, generates a warning prompt to alert the surgeon of an onset or possible onset of non-linear deformation of the retracted tissue; and transmits the warning prompt via the feedback module 150 (e.g., by an auditory, visual, and/or haptic signal).

In particular, after the calibration period, the system 100 initiates a surgical time period for data capture (e.g., activated by a set of conductive tabs on the system 100 coming into contact with patient tissue) by the force sensor 130 and the inertial sensor 140; and, during the surgical time period, the system 100 can continuously or intermittently (e.g., at regular and/or irregular intervals, such as 6 Hertz or 60 Hertz) track force magnitudes of the force applied by the retractor tip 107 to the tissue based on force signals received from the force sensor 130 and track inertial values of the retractor tip 107 based on inertial signals received from the inertial sensor 140.

In one implementation, the system 100 can set up one or more thresholds described herein (e.g., linear deformation force threshold, maximum force threshold, historical data-driven threshold, and/or deviation threshold); and generate and transmit a different warning prompt for each threshold. For example, the system 100 can flash: a yellow light for a first type of threshold; a red light for a second type of threshold; and a red light plus a vibration pattern for a third type of threshold. Accordingly, a surgeon may recognize which threshold is or will be exceeded and may act accordingly, such as by: adjusting, removing, and/or replacing the surgical retractor 105 in order to prevent further tissue damage; electing to perform the surgery with less visibility of a target tissue in order to prevent further tissue damage; or electing to intentionally damage the tissue in order to improve visibility or gain greater access to the target tissue, but now with improved understanding of the risks involved with such a decision.

In addition, the system 100 can incorporate redundant safety precautions by implementing more than one threshold for a single surgical procedure, thereby further minimizing inadvertent damage to retracted tissues.

For example, the control module 160 can generate and transmit more than one warning prompt relating to the same threshold. More specifically, the control module 160 can output (e.g., transmit) a first warning prompt in response to the applied force approaching the force threshold; and transmit a second warning prompt in response to the applied force exceeding the force threshold. In particular, the control module 160 is configured to: track force magnitudes of the force applied by the retractor tip 107 to the tissue during a first time period (i.e., surgical time period) based on the force signal received from the force sensor 130; detect the force applied by the retractor tip 107 approaching a force threshold, the force threshold based on a relationship between force applied by the retractor tip 107 to the tissue and deflection of the retractor tip 107 against the tissue; in response to the force applied by the retractor tip 107 to the tissue approaching the force threshold, generate a first warning prompt indicating a possibility of damage to the tissue; and output the first warning prompt via the feedback module 150. The control module 160 is further configured to: generate a second warning prompt in response to detecting the force magnitude applied by the retractor tip 107 to the tissue exceeding the force threshold, the second warning prompt indicating damage to the tissue; and output the second warning prompt via the feedback module 150, the second warning prompt differing from the first warning prompt.

Blocks of the method S100 further recite: generating a second warning prompt in response to detecting the force applied by the retractor tip 107 to the tissue exceeding the force threshold, the second warning prompt indicating damage to the tissue; and outputting the second warning prompt, the second warning prompt differing from the first warning prompt. Accordingly, the system 100 can provide the surgeon with various levels of contextual feedback, enabling the surgeon to make fully informed decisions regarding force magnitudes experienced by retracted tissues.

6.3 Stress Relaxation of Tissue

In one implementation, the control module 160 can adjust one or more of the thresholds during a surgical procedure based on a stress relaxation of a retracted tissue. When a tissue experiences an applied force over a prolonged interval of time, the tissue can undergo "stress relaxation," which is a reduction in stress at a constant level of strain. More specifically, stress relaxation of the tissue can shift the force-displacement curve of a retracted tissue. Accordingly, the control module 160 shifts the thresholds calculated during calibration to improve the detection of non-linear deformation of the retracted tissue.

The control module 160 can implement one or more of the calibration methods described herein to recalculate force and/or deviation thresholds in real-time during a surgical procedure by using force-displacement values captured during the surgical procedure. In particular, the control module 160 is configured to: dynamically update the force-displacement curve (calculated during the calibration period) based on force magnitudes from the force sensor 130 and orientations from the inertial sensor 140 during a second time period succeeding the first time period (e.g., the first time period and the second time period both occur during the surgical procedure); and adjust the force threshold based on the updated force-displacement curve, the adjusted force threshold indicating an adjusted onset of non-linear deformation of the tissue after experiencing stress-relaxation during the first time period.

Blocks of the method S100 recite: dynamically updating the first force-displacement curve based on the force magnitudes and the orientations during a second time period succeeding the first time period; and adjusting the force threshold based on the updated force-displacement curve, the adjusted force threshold indicating an adjusted onset of non-linear deformation of the tissue after experiencing stress-relaxation during the first time period. Accordingly, the control module 160 can account for stress relaxation of a retracted tissue and adjust one or more thresholds mid-surgery to avoid triggering a false alert or warning prompt that the tissue is approaching or experiencing linear deformation (meanwhile the retracted tissue is not actually near linear deformation). Thus, the surgeon may perform the surgical procedure with reassurance that the system 100 is reliably and accurately providing warning prompts only when necessary (i.e., when an onset or possible onset of tissue damage is occurring).

6.4 Feedback

Generally, the control module 160 is configured to: detect a force magnitude applied to a retracted tissue nearing, meeting, and/or exceeding a force and/or deviation threshold (e.g., set during calibration of the system 100) at a particular time during retraction; and, at approximately the same time, drive a feedback module 150 within the system 100 to output a visual, auditory, and/or vibratory signal to the surgeon indicating, for example, an onset or possible onset of non-linear deformation or possible fracture of the tissue. For example, the control module 160 can drive an actuator in the feedback module 150 to output a warning prompt that includes a vibration (e.g., a low-amplitude vibration) in response to detecting that a force and/or deviation threshold has been exceeded. Additionally and/or alternatively, the control module 160 can drive a speaker or other audio actuator to output a warning prompt that includes an audio warning in response to detecting that a force and/or deviation threshold has been exceeded. Thus, the control module 160—in cooperation with the instrumented retractor—can notify the surgeon of damaging or potentially damaging stresses on the retracted tissue in real-time, thereby enabling the surgeon to adjust the force magnitude applied by the retractor in order to avoid inadvertent damage to and/or further damage to the retracted tissue.

In one implementation, the control module 160 can output (e.g., trigger) the warning prompt in response to the force applied to the retracted tissue exceeding a force and/or deviation threshold modified by a safety factor (i.e., a sensitivity threshold). In particular, the control module 160 can modify the force and/or deviation threshold according to inputs and/or instructions provided by the surgeon, thereby enabling the surgeon to adjust the sensitivity of the threshold based on a real-time manual assessment of the patient. For example, the surgeon may decrease the sensitivity when operating on elderly patients or patients otherwise presenting an increased risk of inadvertent tissue damage during retraction.

In one implementation, the system 100 can include a set of wireless transceivers configured to transmit force magnitudes and orientations to an external computer system configured to execute Blocks of the method S100. Additionally and/or alternatively, the system 100 can include the set of wireless transceivers configured to transmit force magnitudes and orientations to an external computer system configured to plot the retractor's angular displacement against force magnitudes applied to the retracted tissue in real-time on a display (e.g., a monitor or tablet in view of the surgeon).

In these implementations in which the control module 160 defines and/or interfaces with an external computer system, the warning prompt can include a visual notification indicating potential tissue damage and/or observed tissue damage. Blocks of the method S100 recite: transmitting the force magnitudes and the orientations to an external computer system configured to: display the first force-displacement curve against a first background color in response to the force magnitudes falling below the force threshold; display the first force-displacement curve against a second background color in response to the force magnitudes approaching the force threshold; and display the first force-displacement curve against a third background color in response to the force magnitudes exceeding the force threshold, indicating non-linear deformation of the retracted tissue.

For example, the control module 160—in cooperation with the external computer—can plot the retractor's angular displacement against force applied to the retracted tissue in real-time on a display (e.g., a monitor or tablet in view of the surgeon). The system 100 can then display a visual notification in response to the applied force approaching, meeting, and/or exceeding the threshold. For example, the system 100 can: display the force-displacement curve against a first background color (e.g., green) at applied force substantially below the threshold; display the force-displacement curve against a second background color (e.g., yellow) at applied force that approaches the threshold; and display the force-displacement curve against a third background color (e.g., red) at applied force that exceeds the threshold (e.g., observed and/or calculated tissue damage). The system 100 can thus display, in real time, a force-displacement curve representing forces on a retracted tissue and pair the displayed force-displacement curve with visual cues to the surgeon indicating (possible) tissue damage.

In particular, the system 100 can include: a set of wireless transceivers configured to transmit the force magnitudes and the orientations to an external computer system, the external computer system including a display configured to: display the force-displacement curve against a first background color in response to the force magnitudes falling below the force threshold (e.g., green); display the force-displacement curve against a second background color in response to the force magnitudes approaching the force threshold (e.g., yellow); and display the force-displacement curve against a third background color in response to the force magnitudes exceeding the force threshold (e.g., red), indicating non-linear deformation of the retracted tissue.

Additionally and/or alternatively, the system 100 can include: a set of LED indicators 170 configured to activate based on the force magnitudes and the orientations. More specifically, the set of LED indicators 170 can activate in a first color in response to the force magnitudes falling below the force threshold (e.g., green); activate in a second color in response to the force magnitudes approaching the force threshold (e.g., yellow); and activate in a third color in response to the force magnitudes exceeding the force threshold (e.g., red), indicating non-linear deformation of the retracted tissue. In one example, the system 100 can sync the colors of the set of LED indicators 170 with the background colors displayed on the display of the external computer system.

Thus, the instrumented retractor, in cooperation with the control module 160, can promptly issue visual, haptic, and/or audio warnings to the surgeon upon detecting applications of force associated with observed tissue damage (e.g., based on past procedures and/or in response to detecting tissue damage in the current procedure), thereby enabling the surgeon to either avoid damaging the tissue (e.g., by operating with a more limited field of view), or intentionally cause an understood and/or quantifiable amount of tissue damage necessary to achieve a particular field of view to safely complete the procedure and recommend post-operative recovery methods based on the type and/or amount of tissue damage.

6.5 Oxygen Levels

In one implementation, the system 100 can: monitor blood oxygen levels of a tissue retracted by a surgical retractor 105; calculate an amount of time of ischemia (i.e., inadequate blood supply) of the retracted tissue; and prompt the surgeon to hold, remove, or adjust the surgical retractor 105 accordingly. Pressure applied to the tissue retracted by the surgical retractor 105 can reduce an amount of blood flow to an area of the tissue and, thus, reduce oxygenation of the tissue, which could lead to possible tissue damage and/or tissue death, surgical complications, and/or slower healing and recovery times for the patient. By monitoring blood oxygen levels of the retracted tissue, the system 100 can improve patient and surgical outcomes.

In particular, the system 100 can include: a pulse oximeter 145 configured to measure a level of oxygenation of the tissue (e.g., by passing beams of light through the blood of the tissue and measuring changes of light absorption in the blood); and wherein the control module 160 is further configured to generate a warning prompt in response to the level of oxygenation dropping below an oxygen threshold (e.g., below 90% oxygen saturation), the warning prompt indicating a possibility of ischemia of the tissue; and output the warning prompt via the feedback module 150 (e.g., with a haptic, visual, and/or audio signal that may differ from the other types of warning prompts described herein). In response to the warning prompt, the surgeon may adjust the surgical retractor 105 and/or remove and execute a subsequent retraction move to reposition the surgical retractor 105 against the tissue. Accordingly, the control module 160 can re-calibrate the force thresholds based on the new position and/or orientation of the surgical retractor 105 or continue to implement the force thresholds from the initial calibration of the surgical retractor 105.

Additionally and/or alternatively, the control module 160 can apply a safety factor to the oxygen threshold (i.e., reduce the threshold by a defined percentage or number) to reduce a possibility of damage to the retracted tissue due to ischemia.

In addition, oxygen levels of a tissue can vary across the area of tissue in contact with the surgical retractor 105. For example, areas of the retracted tissue closer to edges of the surgical retractor 105 and/or positioned against curved portions of the surgical retractor 105 can experience higher levels of retraction pressure and, thus, high levels of ischemia. Accordingly, in one implementation, the system 100 can include several pulse oximeters 145, each positioned at different locations on the surgical retractor 105 (e.g., along the edges and/or curves of the surgical retractor 105).

Blocks of the method S100 recite: measuring a level of oxygenation of the tissue (e.g., by pulse oximetry); and generating a warning prompt in response to the level of oxygenation dropping below an oxygen threshold (e.g., below 90% oxygen saturation), the warning prompt indicating a possibility of ischemia of the tissue; and outputting the warning prompt (with a haptic, visual, and/or audio signal that may differ from the other types of warning prompts described herein).

Accordingly, the system 100 can provide feedback to a surgeon during a surgical procedure and monitor blood flow and oxygenation of a retracted tissue.

6.6 Characterization of Tissue Damage

In one implementation, in response to detecting non-linear deformation of tissue during a retraction move, the control module 160 can identify the type of tissue damage and/or quantify an amount of tissue damage caused during retraction. The control module 160 can sum (e.g., integrate) forces applied to the retracted tissue over a subsequent period of time in which non-linear deformation is detected in order to determine the total amount of excess retractive force applied to the tissue under non-linear deformation. The control module 160, or an external computer system cooperating with the control module 160, can then indicate the total excess force applied under non-linear deformation and the time period in which this force was applied to the tissue (e.g., at a user interface portal), thereby enabling the surgeon to estimate the extent of damage caused by excess force on the tissue.

In one example, in response to detecting non-linear deformation of the retracted tissue (e.g., based on a first force-displacement curve plotted during initial retraction of the tissue during calibration), the control module 160 can: prompt the surgeon to replace the retracted tissue (e.g., reverse the initial retraction move); subsequently prompt the surgeon to execute a second, similar retraction move; generate (e.g., plot) a second force-displacement curve for tissue based on angular displacement and force data captured during the second retraction move; calculate a difference in elasticity of the tissue between the initial retraction move and the second retraction move based on a comparison between the first force-displacement curve and the second force-displacement curve (e.g., a difference in slope); and estimate (e.g., calculate, identify) an amount and/or type of tissue damage based on the difference in elasticity.

Blocks of the method S100 recite: in response to detecting the force applied by the retractor tip 107 exceeding the force threshold, generating and transmitting a prompt to remove the surgical retractor 105 from the retracted tissue; subsequently generating and transmitting a prompt to reposition the surgical retractor 105 at the tissue; plotting a second force-displacement curve for the tissue based on the force magnitudes and the orientations during a second time period succeeding the repositioning of the surgical retractor 105; calculating a difference in elasticity of the tissue between the first time period and the second time period based on a comparison between the first force-displacement curve and the second force-displacement curve; and estimating an amount of damage to the tissue based on the difference in elasticity.

Furthermore, the control module 160 can identify a type of tissue damage based on an observed step change (e.g., discontinuity) in the force-displacement curve generated during tissue retraction. In particular, the control module 160 can associate the observed step change with detachment of a muscle or tendon from its origin and/or rupture of associated connective tissues (e.g., outside the surgical field of view). Blocks of the method S100 recite: identifying an observed step change in the first force-displacement curve during the first time period; and associating the observed step change with a particular type of tissue damage.

The control module 160 can then provide information on the type and/or amount of tissue damage to the surgeon during or after the procedure, thereby enabling the surgeon to: repair damaged tissues, if feasible; recommend and/or prescribe post-operative recovery methods based on the type and/or amount of damage to the particular tissue, such as a type, frequency and duration of physical therapy; and, more generally, account for the type and/or amount of inadvertent damage to retracted tissues when characterizing an invasiveness of the procedure.

6.7 Pre-Configured Sensitivity

In one implementation, the system 100 can include an integrated peripheral attachment configured to transiently attach to an existing surgical retractor before or during a surgical procedure, wherein the system 100 is pre-configured based on a defined sensitivity or safety factor. Before or during a surgical procedure, a surgeon may select a pre-configured system 100 specific to a patient with certain parameters (e.g., age, gender, weight, etc.) or medical history factors (e.g., degenerative muscle disease, emergency room trauma patient, etc.). For example, a system 100 can be pre-configured with a 0% sensitivity for a standard surgery, a 10% sensitivity for a surgery on an elderly person (in which damage to retracted tissue and/or surgical complications may be more likely to occur and/or post-surgical healing and recovery may occur more slowly), a 20% sensitivity for a surgery on an elite athlete (in which preserving optimal health and performance of the patient's tissue(s) and/or minimizing post-surgical healing and recovery times are a high priority), a 30% sensitivity for a surgery on a patient with a degenerative muscle disease (in which severe damage to retracted tissue and/or surgical complications may be more likely to occur and/or post-surgical healing and recovery may occur more slowly), or a −10% sensitivity for an emergency surgery on a patient (e.g., a patient in a high-risk scenario in which preserving the patient's life has a higher priority than minimizing damage to the patient's retracted tissue(s)).

In particular, the system 100 can include: a housing body 110; an attachment mechanism 120 configured to attach the housing body 110 to the surgical retractor 105, the surgical retractor 105 including a retractor beam 106 and a retractor tip 107 at a distal end of the retractor beam 106; a force sensor 130 configured to output a force signal representing a magnitude of a force applied to the tissue via the retractor tip 107; an inertial sensor 140 configured to output an inertial signal representing orientation of the retractor tip 107; and a feedback module 150. The system 100 further includes a control module 160 configured to: track force magnitudes of the force applied by the retractor tip 107 to the tissue during a first time period based on the force signal received from the force sensor 130; detect the force applied by the retractor tip 107 approaching a force threshold, the force threshold based on a relationship between force applied by the retractor tip 107 to the tissue and deflection of the retractor tip 107 against the tissue; in response to the force applied by the retractor tip 107 to the tissue approaching the force threshold, generating a first warning prompt indicating a possibility of damage to the tissue; and outputting the first warning prompt via the feedback module 150.

In one implementation, the system 100 can further include a set of wireless transceivers configured to transmit force magnitudes and orientations to an external computer system configured to plot the retractor's angular displacement against force magnitudes applied to the retracted tissue in real-time on a display (e.g., a monitor or tablet in view of the surgeon). In these implementations, the system 100 can display force-displacement values; and provide a visual notification in response to the applied force approaching, meeting, and/or exceeding the threshold. Additionally and/or alternatively, a surgeon may use more than one system 100 during a surgical procedure on a patient. In this example, the system 100 can display force-displacement values corresponding to each individual system 100 (e.g., by designating each with a visual indicator and/or system 100 identifier on the display), thereby enabling the surgeon to identify which force-displacement values correspond to which system 100 being used to retract tissue.

Each pre-configured system 100 can have one or more identifying markings on the housing body 110 that indicate the corresponding sensitivity of the system 100 (e.g., a green marking for a standard sensitivity, a yellow marking for a 10% sensitivity, a purple marking for a 20% sensitivity, and a red marking for a −10% sensitivity, etc.). Accordingly, a surgeon may conveniently select a pre-configured system 100 for the patient undergoing the surgical procedure.

7. Tracking Force & Linear Displacement

In another implementation, the system 100 tracks: force magnitudes of the force applied by the retractor tip 107 to the retracted tissue (e.g., based on force signals by a force sensor 130 in contact with the retracted tissue); and concurrent orientations of the retractor tip 107 against the retracted tissue (e.g., based on inertial signals by an inertial sensor 140). The system 100 calculates linear displacement of the retractor tip 107 based on changes in orientation of the retractor tip 107 between sampling intervals during the surgical procedure. Based on the force magnitudes and the orientations, the system 100 can plot a force-displacement curve; monitor a force magnitude applied to the retracted tissue; and generate and transmit a warning prompt in response to the applied force approaching, meeting, and/or exceeding a determined force threshold, indicating possible damage to the retracted tissue. This example system 100 can implement methods described herein to calibrate and set one or more force thresholds; monitor force and linear displacement; and generate and transmit one or more warning prompts accordingly.

For example, when the surgeon retrieves the system 100 and places the system 100 in contact with the target tissue, the impedance across the two electrodes on the body may drop, thereby triggering the control module 160 to activate. Once active, the control module 160 can: sample an initial set of force magnitudes from the force sensor 130 over an initial sampling interval (e.g., two seconds) immediately following contact between the body of the system 100 and the target tissue. The control module 160 can then average the initial set of force magnitudes to calculate a baseline force magnitude for the current application of the system 100. The controller module can: read a timeseries of linear acceleration and angular velocity values from the inertial sensor 140 (e.g., a six-axis IMU including a three-axis accelerometer and a three-axis gyroscope); implement dead reckoning techniques to estimate a total linear displacement of the retractor tip 107 over time (e.g., for up to one minute while the surgeon tightens the retractor tip 107 against the target tissue); calculate a timeseries of linear displacements of the retractor tip 107 from an initial position of the retractor tip 107 based on total linear displacements thus derived from this timeseries of linear acceleration and angular velocity values; concurrently sample force magnitudes from the force sensor 130; and subtract the baseline force magnitude from these force magnitudes to calculate a timeseries of normalized force magnitudes applied to the target tissue. The control module 160 can then implement methods and techniques described above to calibrate a force-displacement curve (e.g., a force magnitude versus linear displacement curve) and/or predict damage to the target tissue based on the timeseries of normalized force magnitudes and the timeseries of linear displacements.

8. Tracking Torque & Angular Displacement

Blocks of the method S100 recite: during retraction of tissue over a first period of time, measuring a sequence of magnitudes of a force applied to a distal end of a retractor in Block S110; and concurrently measuring a corresponding sequence of angular displacements of the retractor in Block S112. Generally, the system 100 is configured to: sample magnitudes (e.g., time-varying magnitudes) of forces applied to the retractor beam 106 by a surgeon to lift and/or lever tissue away from the surgical target at a sequence of times during tissue retraction; concurrently sample a corresponding angular displacement and/or orientation of the retractor beam 106 relative to a point of contact within the wound at each time in the sequence of times; and pair a force magnitude with a corresponding angular displacement for each time in the sequence of times. For example, during a total hip arthroplasty (e.g., hip replacement), the system 100 can monitor forces applied to the end of a levered retractor (e.g., a Hohmann-style retractor) during separation of the *piriformis* musculotendinous complex from the hip. In particular, a force sensor 130 within a beam load cell attached to the retractor can sample a sequence of force magnitudes applied to the retractor by the surgeon continuously and/or at a particular sampling frequency (e.g., 5 Hz, 25 Hz). Concurrently, a gyroscope, accelerometer 140, or level attached to the retractor can detect the angular displacement of the retractor relative to the hip (e.g., at the same sampling frequency), which is generally proportional (e.g., linearly, inversely) to a linear displacement of the *piriformis* from the hip.

Blocks of the method S100 further recite transforming the sequence of force magnitudes into a sequence of torques applied to the tissue by a tip of the retractor in Block S114. Generally, the system 100 is configured to detect a lever arm (e.g., lever distance) defined by the distance between the point of load application to the retractor and the retractor's point of contact and multiply the sequence of force magnitudes by the lever arm in order to calculate a sequence of torques applied to the tissue by the retractor tip 107. In particular, a remote distance meter 125 (e.g., a laser distance meter) can continuously and/or intermittently detect (e.g., sample, monitor) a distance between the remote distance meter 125 and the retractor's contact point. The control module 160 can then scale force magnitudes sampled at the beam load cell 130 by a corresponding lever distance, thereby yielding the magnitude of torque applied to the tissue at each sampling time. For example, during a total hip arthroplasty, a laser distance meter affixed to an instrumented Hohmann-style retractor can continuously sample the lever distance between the end of the retractor beam 106 and the retractor's point of contact with the hip (e.g., anchor point, fulcrum) and/or sample a sequence of such lever distances during retraction of the *piriformis* musculotendinous complex. The control module 160 can then multiply the sequence of force magnitudes at the beam load cell 130 by corresponding lever distances in order to transform force magnitudes applied to the retractor beam 106 (e.g., by the surgeon) into torques applied to the *piriformis* itself during retraction.

Blocks of the method S100 further recite calculating a rate of change of the applied torque as a function of angular displacement of the retractor in Block S116. Generally, the control module 160 is configured to derive an initial rate of change in the force and/or torque applied to the tissue with respect to angular displacement and/or orientation of the retractor over a first period of time during retraction of the tissue based on the sequence of angular displacements and the sequence of applied torques. For example, the control module 160 can generate a plot and/or curve representing the angular displacement of the retractor responsive to applications of force to the retractor beam 106 as a function of torque applied to the tissue by the retractor tip 107 effected by these applications of force. Because the angular displacement of the retractor is proportional to the linear displacement and/or deformation of the tissue in contact with the retractor tip 107, the plot generally defines a stress-strain relationship (e.g., a stress-strain curve) for the particular tissue, representing displacement and/or deformation of the retracted tissue (e.g., strain) responsive to applications of force and/or torque to the tissue by the retractor. At low to moderate displacements of the tissue, such as during initial application of torque by the retractor, the rate of change of applied torque is generally a linear function of the angular displacement and/or orientation of the retractor that represents elastic deformation of the tissue. Therefore, the control module 160 can: calculate the rate of change of the torque and/or force applied to the tissue based on a slope (e.g., an initial slope) of the plot and/or stress-strain curve over an initial period of time (e.g., during initial application of torque by the retractor); and associate the slope with an observed nominal (e.g., normal, healthy) elasticity of the tissue responsive to changes in the retractor orientation. Thus, the control module 160 can correlate a particular observed stress-strain relationship or portion of a stress-strain curve with (non-damaging) elastic deformation of a tissue in contact with the retractor.

Blocks of the method S100 further recite: at a second time succeeding the first period of time, during retraction of the tissue, detecting a decrease in the rate of the change of the applied torque relative to angular displacement of the retractor in Block S120. Generally, the control module 160 is configured to: calculate an updated rate of change of the torque applied to the tissue by the retractor tip 107 based on the retractor's angular displacement and torque applied to the tissue sampled at a later time during retraction; and, in response to detecting that the updated rate of change is inconsistent with (e.g., less than) the initial range of change associated with nominal tissue elasticity, generate (e.g., output) an auditory, visual, and/or tactile prompt to the surgeon indicating dangerous and/or damaging stresses on the tissue. In particular, at higher displacements of the tissue (e.g., when the tissue is substantially retracted), the controller can detect a torque magnitude and angular displacement captured at a particular time, represented by a point on the stress-strain curve, that falls below and/or changes the initial slope of the stress-strain curve associated with nominal elasticity of the tissue, indicating a possible non-linear deformation and/or decrease in elasticity of the retracted tissue. The control module 160 is also configured to detect, record, and/or report step changes (e.g., discontinuities) in the stress-strain curve, which can indicate rupture in tendinous connections between the tissue and bone or cartilage, or cracks in bone and/or cartilage at the point of contact with the retractor beam 106.

For example, during retraction of the *piriformis* musculotendinous complex, the control module 160 can—in cooperation with an instrumented Hohmann-style retractor—plot calculated values of torques applied to the *piriformis* by the retractor tip 107 as a function of the angular displacement of the retractor; calculate an initial slope of the resulting stress-strain curve associated with nominal elastic displacement of the *piriformis*; and subsequently detect a decrease in the slope of the curve, an inflection point in the curve, and/or an angular displacement and torque magnitude that falls below the slope of the curve that may correspond to non-linear deformation (e.g., reduced elasticity) of the *piriformis* and therefore damage to the *piriformis* muscle belly (e.g., at the point of contact with the retractor tip 107), damage to the *piriformis* muscle origin at the sacrum, and/or damage to musculotendinous connections (e.g., outside the surgical field of view).

Thus, the control module 160 can detect inadvertent damage—or the possibility of inadvertent damage—to tissue in response to forces and/or torques applied by the retractor in near-real time at any point during the retraction move. At approximately the same time, the control module 160 can serve (e.g., output, provide) an audio, visual, and/or tactile notification to the surgeon indicating possible tissue damage and prompting the surgeon to reduce application of force to the retractor.

8.2 Feedback

Blocks of the method S100 further recite: in response to the first rate of change falling below the initial rate of change, generating a warning prompt indicating possible damage to the tissue in Block S130. Generally, the control module 160 is configured to: detect a decrease in the rate of change of the torque applied to the tissue relative to an increase in the angular displacement of the retractor at a particular time during retraction (e.g., a decreased slope and/or inflection point of the stress-strain curve); and, at approximately the same time, drive a feedback module 150 within the retractor to output an auditory and/or vibratory signal to the surgeon indicating entry and/or possible entry of the tissue into non-linear deformation. For example, the control module 160 can drive an actuator in a haptic feedback module 150 within the grip affixed to the retractor to output a warning prompt that includes a vibration (e.g., a low-amplitude vibration) in response to detecting decreased elasticity of the tissue. Additionally and/or alternatively, the control module 160 can drive a speaker or other audio actuator located on the retractor (e.g., on the grip) to output a warning prompt that includes an audio warning in response to detecting decreased elasticity of the tissue. Thus, the control module 160—in cooperation with the instrumented retractor—can notify the surgeon of damaging or potentially damaging stresses on the retracted tissue in real time, thereby enabling the surgeon to adjust the force magnitude applied to the retractor in order to avoid inadvertent damage to and/or further damage to the retracted tissue.

In one implementation, the control module 160 can output (e.g., trigger) the warning prompt in response to the decrease in rate of change exceeding a predefined sensitivity threshold value. In particular, the control module 160 can modify this sensitivity threshold according to inputs and/or instructions provided by the surgeon, thereby enabling the surgeon to adjust this threshold sensitivity for based on a real-time manual assessment of the patient. For example, the surgeon may decrease the threshold sensitivity when operating on elderly patients or patients otherwise presenting an increased risk of inadvertent tissue damage during retraction.

In another implementation, the control module 160 can additionally and/or alternatively generate the warning prompt in response to a magnitude of force applied to the retractor and/or a magnitude of torque applied by the retractor tip 107 exceeding a threshold magnitude. In one example, the threshold magnitude can be set by the control module 160 and/or the surgeon to be an upper bound on a range of retractive force and/or torque magnitudes demonstrated in medical literature to be non-damaging to the particular retracted tissue (e.g., 3.0 Nm for the *piriformis* musculotendinous complex).

In another example, the control module 160 can calculate the threshold magnitude based on stress-strain data generated for the particular tissue during previous procedures. For example, the control module 160 can: access (e.g., from cloud storage, from local memory) stress-strain data generated during retraction of the particular tissue in previous operations on patients of a similar demographic (e.g., age, gender, weight); identify a subset of stress-strain data corresponding to procedures in which tissue damage occurred during retraction (e.g., based on stress-strain curves generated during each procedure); and set the threshold magnitude based on force and/or torque magnitudes observed to cause and/or correspond to tissue damage (e.g., an average magnitude, the lowest magnitude). Thus, the control module 160—in cooperation with the instrumented retractor—can output a warning prompt in response to detecting a force magnitude applied to the retractor and/or a torque magnitude applied to the retracted tissue that approaches or exceeds a threshold magnitude observed to be associated with tissue damage in previous procedures, even if the control module 160 has not yet detected tissue damage (e.g., non-linear deformation) during the current procedure.

In another implementation in which the control module 160 defines and/or interfaces with an external computer system, the warning prompt can include a visual notification indicating potential tissue damage and/or observed tissue damage. For example, the control module 160—in cooperation with the external computer system—can plot the retractor's angular displacement against calculated torque magnitudes applied to the retracted tissue in real-time on a display (e.g., a monitor or tablet in view of the surgeon). The system can then display a visual notification in response to the applied force and/or torque approaching the threshold magnitude and/or in response to detecting non-linear deformation of the retracted tissue. For example, the system can: display the stress-strain curve against a first background color (e.g., green) at applied force and/or torque magnitudes substantially below the threshold magnitude; display the stress-strain curve against a second background color (e.g., yellow) at applied force and/or torque magnitudes that approach the threshold magnitude; and display the stress-strain curve against a third background color (e.g., red) in response to detecting non-linear deformation of the retracted tissue (e.g., observed and/or calculated tissue damage). The system can thus display, in real time, a stress-strain curve representing forces and/or torques on a tissue displaced by the retractor and pair the displayed stress-strain curve with visual cues to the surgeon indicating (possible) tissue damage.

Thus, the instrumented retractor, in cooperation with the control module 160, can promptly issue visual, haptic, and/or audio warnings to the surgeon upon detecting applications of force and/or torque magnitudes associated with observed tissue damage in past procedures and/or in response to detecting tissue damage in the current procedure, thereby enabling the surgeon to either avoid damaging the tissue (e.g., by operating with a more limited field of view), or intentionally cause an understood and/or quantifiable amount of tissue damage necessary to achieve a particular field of view to safely complete the procedure and recommend post-operative recovery methods based on the type and/or amount of tissue damage.

8.3 Characterization of Tissue Damage

In one implementation, in response to detecting non-linear deformation of tissue during a retractive move, the control module 160 can identify the type of tissue damage and/or quantify an amount of tissue damage caused during retraction. The control module 160 can sum (e.g., integrate) force and/or torque magnitudes applied to the tissue over a subsequent period of time in which plastic tissue deformation is detected in order to determine the total amount of excess retractive force and/or torque applied to the tissue under non-linear deformation. The control module 160, or an external computer system cooperating with the control module 160, can then indicate the total excess force and/or torque applied under plastic tissue deformation and the time period in which this force and/or torque was applied to the tissue (e.g., at a user interface portal), thereby enabling the surgeon to estimate the extent of damage caused by excess strain on the tissue.

In one example, in response to detecting non-linear deformation of the retracted tissue (e.g., based on a first stress-strain curve plotted during initial retraction of the tissue), the control module 160 can: prompt the surgeon to replace the retracted tissue (e.g., reverse the initial retraction move); subsequently prompt the surgeon to execute a second, similar retraction move; generate (e.g., plot) a second stress-strain curve for tissue based on angular displacement and force data captured during the second retraction move; calculate a difference in elasticity of the tissue between the initial retraction move and the second retraction move based on a comparison between the first stress-strain curve and the second stress-strain curve (e.g., a difference in slope); and estimate (e.g., calculate, identify) an amount and/or type of tissue damage based on the difference in elasticity.

Furthermore, the control module 160 can identify a type of tissue damage based on an observed step change (e.g., discontinuity) in the stress-strain curve generated during tissue retraction. In particular, the control module 160 can associate the observed step change with detachment of a muscle or tendon from its origin and/or rupture of associated connective tissues (e.g., outside the surgical field of view).

The control module 160 can then provide information on the type and/or amount of tissue damage to the surgeon during or after the procedure, thereby enabling the surgeon to: repair damaged tissues, if feasible; recommend and/or prescribe post-operative recovery methods based on the type and/or amount of damage to the particular tissue, such as a type, frequency and duration of physical therapy; and, more generally, account for the type and/or amount of inadvertent damage to retracted tissues when characterizing an invasiveness of the procedure.

9. Other Retractor Geometries

In one variation, the system 100 includes an instrumented forceps-style retractor 105, such as a Meyerding-style or Gelpi-style retractor.

Figure 5:
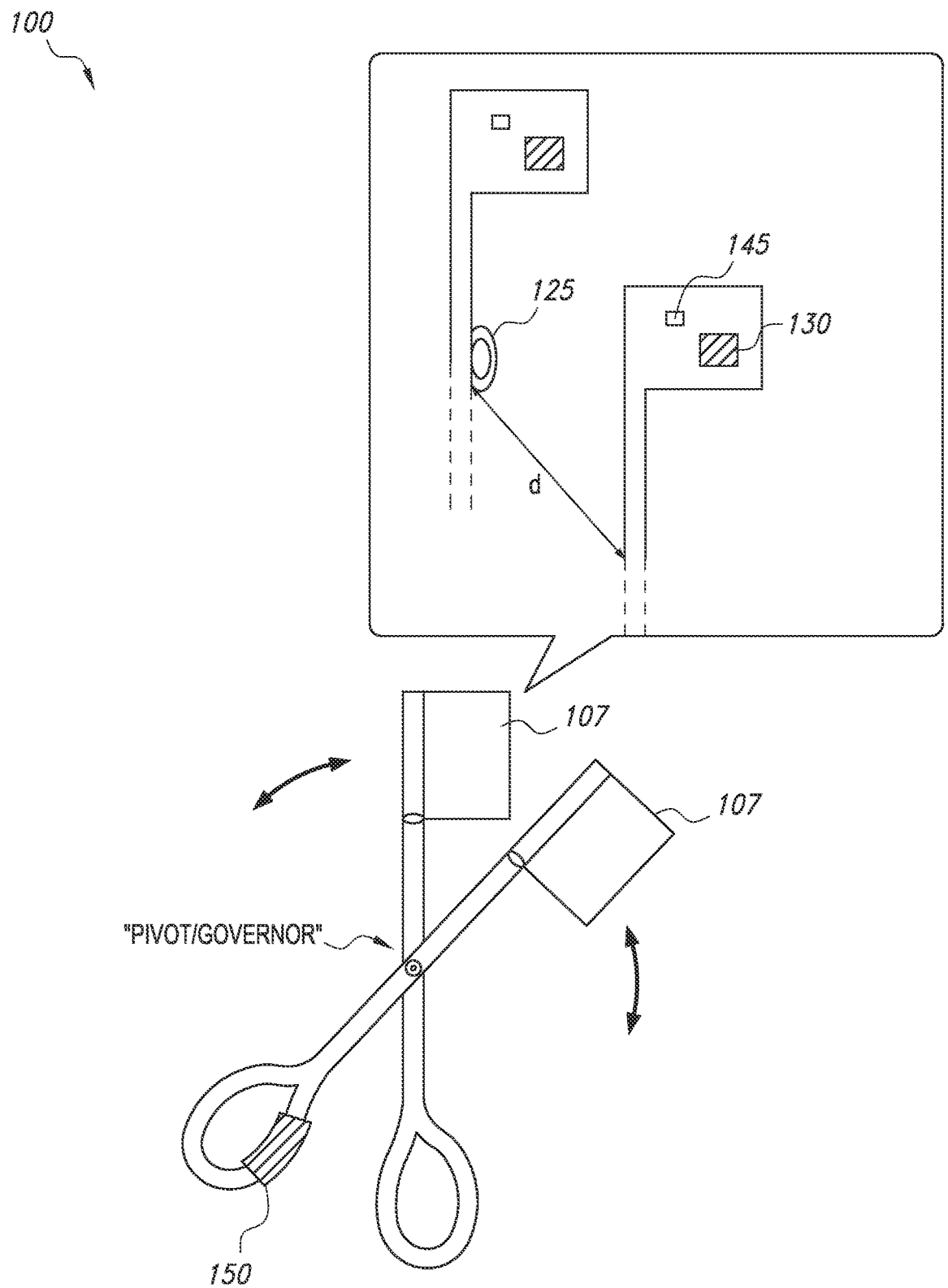
FIG. 5 is a schematic representation of a third variation of the system.

As illustrated in FIG. 5, in this variation, the retractor 105 can define a pair of retractor arms connected about a pivot, wherein each retractor arm includes: a retractor tip 107 (e.g., a broad Meyerding-style tip, a fine Gelpi-style tip) configured for placement against tissues during retraction; and a handle (e.g., a hand grip) opposite the retractor tip 107. Thus, in this variation, expansion or contraction of the handles of the retractor (e.g., by a surgeon) rotates the retractor arms about the pivot and opens (or closes) the retractor tips, thereby displacing (or cinching) tissue adjacent the retractor tips.

Furthermore, in this variation, the instrumented retractor 105 can include: a set of force sensors 130 (e.g., strain gauges, force-sensitive resistive elements) integrated into one or both grips and/or one or both retractor tips of the retractor; a remote distance meter 125 (e.g., laser distance meter) affixed to a grip and configured to detect a distance between the grip and the point of contact between the corresponding retractor tip 107 and a tissue, and/or a separation distance between the two grips; and a haptic and/or audio feedback module 150 integrated with the grip configured to output auditory and/or vibratory signals. In this variation, the instrumented retractor 105 can also include an input mechanism—such as a trigger or a shock—configured to enable (e.g., initiate) recording of data capture by the load cell 130, the accelerometer/gyroscope 140, and the remote distance meter 125. For example, the surgeon may: depress the input mechanism when initiating the retraction move and/or during execution of the retraction in order to enable capture (e.g., collection) of force, orientation, and distance data; and then release the input mechanism when repositioning the retractor, thereby releasing application of force to the retractor beam 106 and thus preventing false-positive feedback.

The instrumented forceps retractor 105 further includes and/or cooperates with a control module 160 configured to execute Blocks of the method S1oo. More specifically, during a retraction move, the control module 160 can continuously and/or intermittently: sample magnitudes of forces detected by the set of force sensors (e.g., applied by a surgeon); sample lever distances between the grip of the retractor and the tip of retractor detected by the remote distance meter 125; and sample separation distances between the retractor grips detected by the remote distance meter 125. The control module 160 can then transform sampled force magnitudes in magnitudes of (e.g., time-varying) torque applied to retracted tissues by the retractor tip 107s by multiplying these force magnitudes by sampled lever distances. The control module 160 can also transform sampled separation distances between the retractor grips into displacements of retracted tissues based on the length of the retractor arms (e.g., as detected by the lever distance). Additionally and/or alternatively, the set of force sensors can be integrated directly into the retractor tip 107s, thereby enabling the control module 160 to directly sample forces applied to tissues by the retractor tip 107s during a retraction move.

Figure 4:
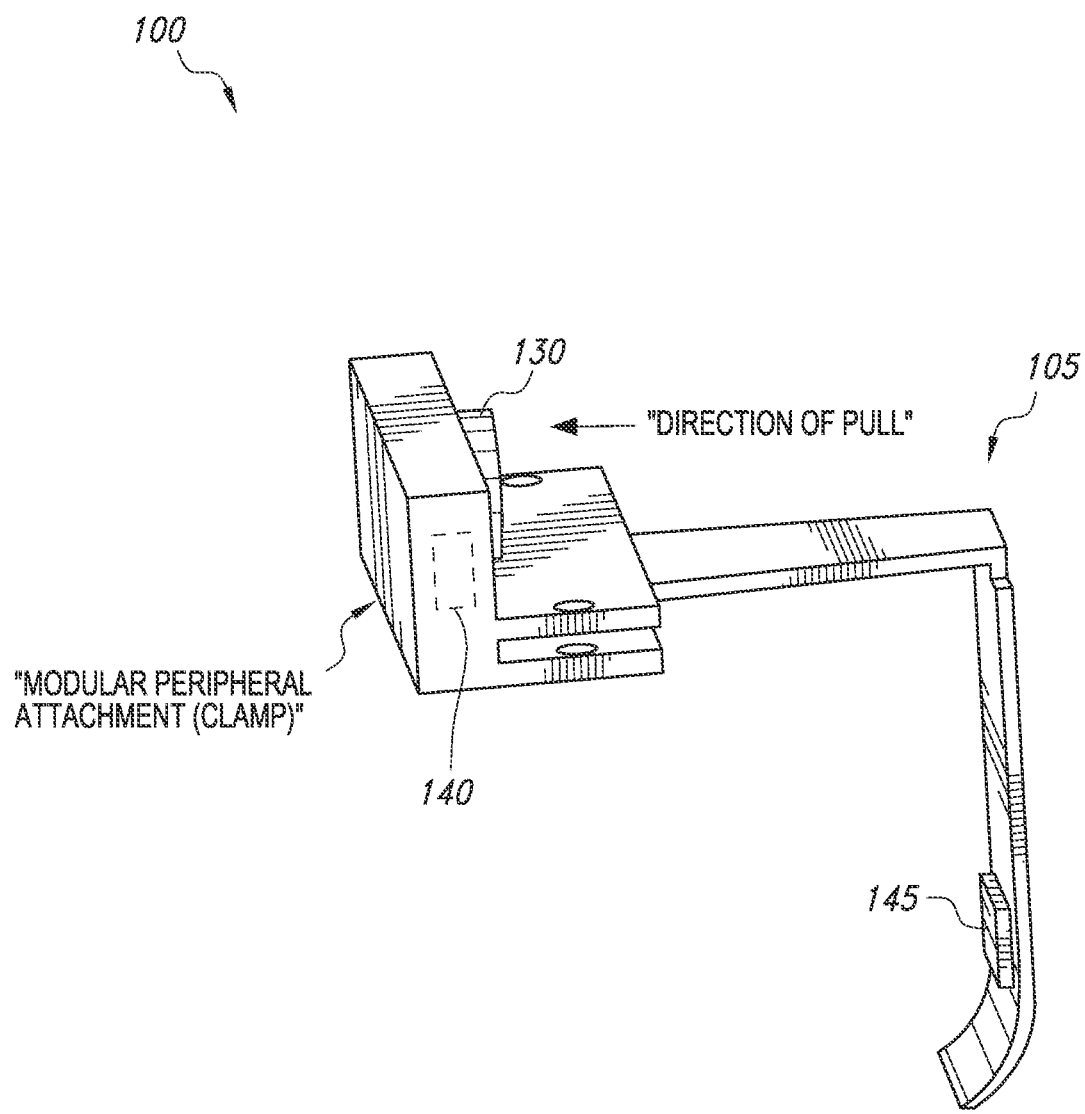
FIG. 4 is a schematic representation of a second variation of the system.

In another variation, and as illustrated in FIG. 4, the system 100 includes an instrumented pulling retractor such as a malleable retractor. In this variation, the pulling retractor can include a set of force sensors 130 integrated into the tip 107 of the retractor 105 or the grip of the retractor and a feedback module 150. A control module 160 affixed to the retractor 105 (or cooperating with the retractor) can then: sample (e.g., monitor) magnitudes of forces applied to tissues during a retraction move and/or while the retractor is held to maintain the surgical field of view; and transform these force magnitudes into pressures applied to retracted tissues based on a known geometry (e.g., area) of the retractor tip 107. Subsequently, the control module 160 can calculate an ischemia time for the retracted tissues based on these force and/or pressure calculations and trigger output of an auditory and/or haptic warning by the feedback module 150 in response to the retraction time approaching the calculated ischemia time, prompting the surgeon to withdraw the retractor in order to restore blood flow to the retracted tissue.

Additionally and/or alternatively, the set of sensors can be integrated into a modular, peripheral attachment configured to transiently attach to an existing base retractor before or during a surgical procedure. The peripheral attachment can include: a remote distance meter 125; a force sensor 130 configured to detect the magnitude of a force applied to the retractor (e.g., at the point of contact with the surgeon); a level or gyroscope configured to detect the orientation of the retractor beam 106; and a set of wireless transceivers configured to transmit force, orientation, and distance data to an external computer system configured to execute Blocks of the method S100. Following the procedure, the peripheral attachment can be disposed of and the base retractor sanitized in preparation for a subsequent surgery.

9.1 Remote Sensor

In one implementation, the system 100 can be configured with a force sensor 130 arranged remotely from the housing body no. In particular, the force sensor 130 can be arranged near the tip of the surgical retractor 105 to contact the tissue retracted by the surgical retractor 105; and transmit (e.g., wirelessly) force signals to the control module 160 of the system 100, which can be arranged along a length of the surgical retractor 105 or near a proximal end of the surgical retractor 105. However, the system 100 can alternatively be configured with the force sensor 130 arranged near a proximal end of the surgical retractor 105 to detect an amount of force applied to the proximal end of the surgical retractor 105, for example, by a surgeon; and correlate the applied force to the force applied to the retracted tissue by the surgical retractor 105. In one implementation, the control module 160 can convert the force applied by the surgeon at the proximal end of the surgical retractor 105 to the force applied by the tip of the surgical retractor 105 at the retracted tissue. In particular, the control module 160 can store a predefined coefficient or scalar value (e.g., based on the geometry for a particular type of surgical retractor) for multiplying the force signals captured by the force sensor 130 into force magnitudes on the retracted tissue.

Additionally and/or alternatively, the system 100 can be configured with an inertial sensor 140 arranged remotely from the housing body 110 and, more specifically, on a distal end of the surgical retractor 105 (towards the tip) to remotely detect a change in orientation of the tip of the surgical retractor 105. For example, the inertial sensor 140 can include a strain gauge, a potentiometer, a laser, and/or an optical position sensor that remotely detects a change in orientation of the retractor tip 107. In particular, the inertial sensor 140 can transmit (e.g., wirelessly) inertial signals to the control module 160 of the system 100, which can be arranged along a length of the surgical retractor 105 or near a proximal end of the surgical retractor 105. In one implementation, the control module 160 can store a predefined coefficient or scalar value (e.g., based on the geometry for a particular type of surgical retractor) for multiplying the inertial signals captured by the inertial sensor 140 into changes in orientation by the retractor tip 107.

This example system 100 can implement methods described herein to calibrate and set one or more force thresholds; capture data (e.g., force and/or torque and angular and/or linear displacement); and generate and transmit one or more warning prompts accordingly.

10. Robotically-Assisted Retraction and Robotic Surgeries

In one variation, Blocks of the method S100 are executed by or in conjunction with a robotic surgical device (e.g., an automated retractor, a (semi) autonomous surgical robot) in order to reduce and/or prevent inadvertent tissue damage during a retraction move. In this variation, the robotic surgical device includes a retractor device (e.g., a levered retractor tool); a set of force sensors 130; a remote distance meter 125; an accelerometer and/or orientation detection device 140; and a control module 160 configured to drive components on the robotic surgical device to automatically execute a range of motions that effect particular retraction moves during a robotically-assisted surgical procedure, as well as monitor forces and/or torques applied to retracted tissues in real time. Thus, the robotic surgical device can be configured to execute Blocks of the method S100 in order to characterize forces exerted with the retractor device and resulting orientations of the retractor device throughout the retraction move; transform forces exerted with the retractor device into torques applied to tissues during execution of a retraction move; transform orientations of the retractor device into displacements of retracted tissues; derive and update a stress-strain relationship for the retracted tissue in real time; and automatically stop or correct the retraction move in response to the stress-strain relationship indicating possible non-linear deformation of the retracted tissue. Furthermore, the robotic surgical device can be configured to limit applications of force and/or torque to magnitudes below predefined threshold magnitudes (e.g., associated with tissue damage) and/or to stop the retraction motion in response to achieving a threshold displacement of the tissue.

Thus, the robotic surgical device can execute Blocks of the Method S100 to electrically or mechanically limit applications of torque and/or displacement of tissues to non-harmful ranges during automatic execution of a retraction move in order to achieve a maximum possible surgical field of view without risking damage to retracted tissues.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

The invention claimed is:

1. A method for predicting potential damage to a tissue within a patient caused by tissue retraction during a surgical procedure, the method comprising:
   during retraction of the tissue by a surgical retractor comprising a retractor beam and a retractor tip during a first time period, accessing a sequence of force signals representing forces applied to the tissue by the retractor tip;
   based on the sequence of force signals, detecting a first sequence of forces applied by the retractor tip to the tissue during the first time period;
   based on the first sequence of forces, detecting a first force applied by the retractor tip to the tissue approaching a first force threshold, the first force threshold based on a relationship between force applied by the retractor tip to tissues and deflection of the retractor tip against tissues;
   in response to the first force applied by the retractor tip to the tissue approaching the first force threshold, generating a first warning prompt indicating possibility of damage to the tissue;
   outputting the first warning prompt;
   accessing a set of force-displacement data representing retraction of tissues during a set of previous surgical procedures on a population patients;
   identifying a subset of force-displacement data, in the set of force-displacement data, indicating damage to tissues during retraction of tissues in the set of previous surgical procedures;
   setting a second force threshold based on forces corresponding to damage to tissues represented in the subset of force-displacement data;
   based on the first sequence of forces, detecting a second force applied by the retractor tip to the tissue approaching the second force threshold;
   in response to the second force applied by the retractor tip to the tissue approaching the second force threshold, generating a second warning prompt indicating damage to the tissue; and
   transmitting the second warning prompt.

2. The method of claim 1, further comprising, during a calibration period preceding the first time period:
   tracking an initial sequence of forces applied by the retractor tip to the tissue based on the sequence of force signals;
   tracking an initial sequence of orientations of the retractor tip based on a sequence of inertial signals output by the surgical retractor during the calibration period;
   plotting a first force-displacement curve based on the initial sequence of forces and the initial sequence of orientations; and
   calculating the first force threshold corresponding to onset of non-linear deformation of the tissue indicated in the first force-displacement curve.

3. The method of claim 2, further comprising:
   generating a second force-displacement curve based on the first sequence of forces applied by the retractor and orientations of the retractor tip during the first time period; and
   updating the first force threshold based on onset of non-linear deformation of the tissue, after experiencing stress-relaxation during the initial time period, indicated in the second force-displacement curve.

4. The method of claim 2, further comprising:
   tracking a first sequence of orientations of the retractor tip during the first time period based on a sequence of inertial signals output by the surgical retractor during the first time period;
   plotting a second force-displacement curve based on the first sequence of forces and the first sequence of orientations during the second time period; and
   in response to the second force-displacement curve deviating from the first force-displacement curve:
       generating a third warning prompt; and
       outputting the third warning prompt.

5. The method of claim 2, further comprising:
   displaying the first force-displacement curve against a first background color in response to a current force, in the first sequence of forces, falling below the first force threshold;
   displaying the first force-displacement curve against a second background color in response to the current force, in the first sequence of forces, approaching the first force threshold; and
   displaying the first force-displacement curve against a third background color in response to the foree-magnitudes current force, in the first sequence of forces, exceeding the first force threshold.

6. The system of claim 1, further comprising:
   detecting an oxygenation level in the tissue;
   generating a third warning prompt in response to the oxygenation level dropping below an oxygenation threshold, the third warning prompt indicating possibility of ischemia of the tissue; and
   outputting the third warning prompt.

7. The method of claim 1, further comprising populating the first warning prompt with a alert to reposition the surgical retractor on the tissue.

8. The method of claim 7, further comprising:
   tracking a second sequence of forces applied by the retractor tip to the tissue during a second time period following repositioning of the retractor tip on the tissue based on the sequence of force signals;
   tracking a second sequence of orientations of the retractor tip during the second time period based on the sequence of inertial signals;
   plotting a second force-displacement curve for the tissue based on the second sequence of forces and the orientations during the second time period;
   calculating a difference in elasticity of the tissue between the calibration period and the second time period based on a difference between the first force-displacement curve and the second force-displacement curve; and
   estimating an amount of damage to the tissue based on the difference in elasticity.

9. A method for predicting potential damage to a tissue within a patient caused by tissue retraction by a surgical retractor during a surgical procedure, the surgical retractor comprising a retractor beam and a retractor tip, the method comprising:
   during a calibration period:
      outputting a first sequence of force signals representing magnitude of forces applied to the tissue via the retractor tip;
      outputting a first sequence of inertial signals representing orientation of the retractor tip;
      tracking a first set of force magnitudes of forces applied by the retractor tip to the tissue based on the first sequence of force signals;
      tracking a first set of orientations of the retractor tip against the tissue based on the first sequence of inertial signals;
      plotting a first force-displacement curve based on the first set of force magnitudes and the first set of orientations;
   during a first time period:
      outputting a second sequence of force signals representing magnitude of forces applied to the tissue via the retractor;
      outputting a second sequence of inertial signals representing orientation of the retractor tip;
      tracking a second set of force magnitudes of forces applied by the retractor tip to the tissue based on the second sequence of force signals;
      tracking a second set of orientations of the retractor tip against the tissue based on the second sequence of inertial signals;
      plotting a second force-displacement curve based on the second set of force magnitudes and the second set of orientations; and
      detecting the second force-displacement curve deviating from the first force-displacement curve; and
      in response to detecting the second force-displacement curve deviating from the first force-displacement curve:
         generating a first warning prompt indicating possibility of damage to the tissue; and
         outputting the first warning prompt.

10. The method of claim 9:
   wherein detecting the second force-displacement curve deviating from the first force-displacement curve comprises:
      detecting a first deviation between the first force-displacement curve and the second force-displacement curve at a first sampling interval during the first time period; and
      detecting a second deviation between the first force-displacement curve and the second force-displacement curve at a second sampling interval succeeding the first sampling interval during the first time period, the second deviation exceeding the first deviation; and
   wherein generating the first warning prompt indicating possibility of damage to the tissue comprises generating the first warning prompt indicating possibility of damage to the tissue based on the second deviation exceeding the first deviation.

* * * * *